United States Patent
Terwilliger

[19]

[11] Patent Number: 6,106,484

[45] Date of Patent: Aug. 22, 2000

[54] REUSABLE AUTOMATED BIOPSY NEEDLE HANDLE

[75] Inventor: Richard A. Terwilliger, Estes Park, Colo.

[73] Assignee: Medical Device Technologies, Inc., Gainesville, Fla.

[21] Appl. No.: 09/170,893

[22] Filed: Oct. 13, 1998

Related U.S. Application Data

[63] Continuation-in-part of application No. 09/132,941, Aug. 11, 1998, which is a continuation-in-part of application No. 09/076,181, May 12, 1998.

[51] Int. Cl.⁷ .................................................. A61B 10/00
[52] U.S. Cl. ............................................................ 600/568
[58] Field of Search ..................................... 600/562, 564, 600/565, 566, 567, 568

[56] References Cited

U.S. PATENT DOCUMENTS

| | | |
|---|---|---|
| Re. 34,056 | 9/1992 | Lindgren et al. . |
| 3,090,384 | 5/1963 | Baldwin et al. . |
| 3,732,858 | 5/1973 | Banko . |
| 3,788,320 | 1/1974 | Dye . |
| 3,844,272 | 10/1974 | Banko . |
| 4,210,146 | 7/1980 | Banko . |
| 4,266,555 | 5/1981 | Jamshidi . |
| 4,403,617 | 9/1983 | Tretinyak . |
| 4,476,864 | 10/1984 | Tezel . |
| 4,570,632 | 2/1986 | Woods . |
| 4,600,014 | 7/1986 | Beraha . |
| 4,640,296 | 2/1987 | Schnepp-Pesch et al. . |
| 4,651,752 | 3/1987 | Fuerst . |
| 4,655,226 | 4/1987 | Lee . |
| 4,699,154 | 10/1987 | Lindgren . |
| 4,733,671 | 3/1988 | Mehl . |
| 4,747,414 | 5/1988 | Brossel . |
| 4,776,346 | 10/1988 | Beraha et al. . |
| 4,817,631 | 4/1989 | Schnepp-Pesch et al. . |
| 4,924,878 | 5/1990 | Nottke . |
| 4,958,625 | 9/1990 | Bates et al. . |
| 5,025,797 | 6/1991 | Baran . |
| 5,064,411 | 11/1991 | Gordon, III . |
| 5,220,926 | 6/1993 | Jones . |
| 5,316,013 | 5/1994 | Striebel, II et al. . |

FOREIGN PATENT DOCUMENTS

| | | |
|---|---|---|
| 0010321 | 4/1980 | Germany . |
| 0141108 | 4/1980 | Germany . |
| 175611 | 9/1965 | Russian Federation . |
| 709714 | 6/1954 | United Kingdom . |
| 748451 | 5/1956 | United Kingdom . |
| WO 83/03343 | 10/1983 | WIPO . |

*Primary Examiner*—Max Hindenburg
*Assistant Examiner*—Brian Szmal
*Attorney, Agent, or Firm*—Fliesler, Dubb, Meyer & Lovejoy LLP

[57] ABSTRACT

A novel automated handle assembly has an opening that allows for insertion of a needle set. The needle set is an integral unit and consists of an outer hollow cannula and an inner pointed tip stylet. The stylet and the cannula are capable of being urged forward separately into the biopsy area in a defined motion in relation to each other. The handle assembly includes a housing, a cannula extension and a stylet extension. In operation, the stylet and the cannula are inserted into the housing. The extensions are slidable and moved rearward separately until the stylet and the cannula are in a spring loaded position wherein first locking members have engaged second locking members on both the stylet and the cannula. The stylet and the cannula are inserted into a patient near the biopsy area. The stylet is then urged into the biopsy area. The stylet extension is pushed forward by a user's thumb and the stylet is fired so that the tissue is pierced. The cannula extension is triggered by the firing of the stylet and automatically urged forward so that the tissue is severed and captured in the notch of the stylet. After disengaging the biopsy area, the stylet is pressed forward using the extension of the stylet so that the tissue sample is exposed and may be removed. The stylet and cannula are then pulled back into the starting position so that multiple samples may be taken. The automated handle assembly may be made of plastic or metal.

20 Claims, 22 Drawing Sheets

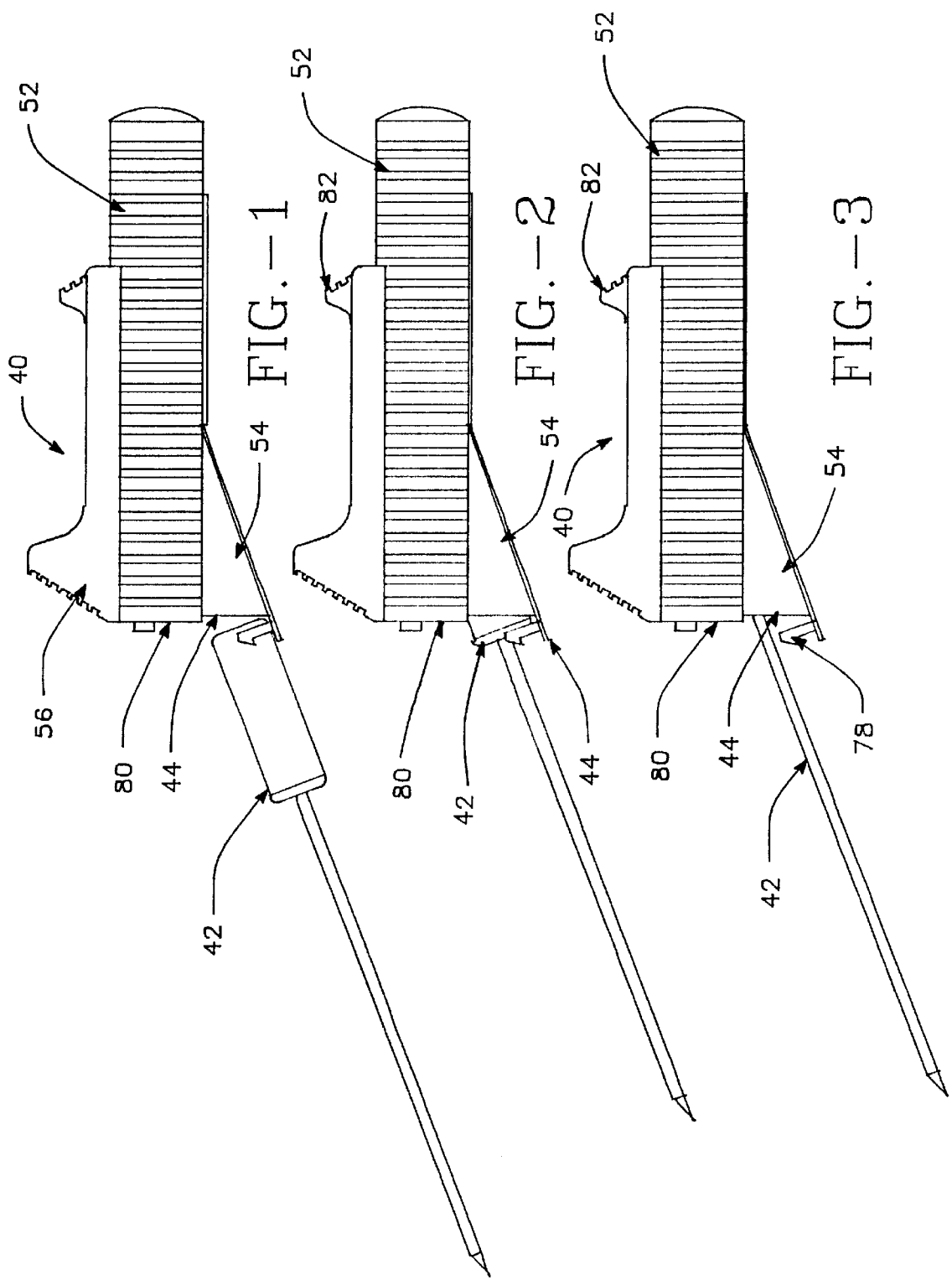

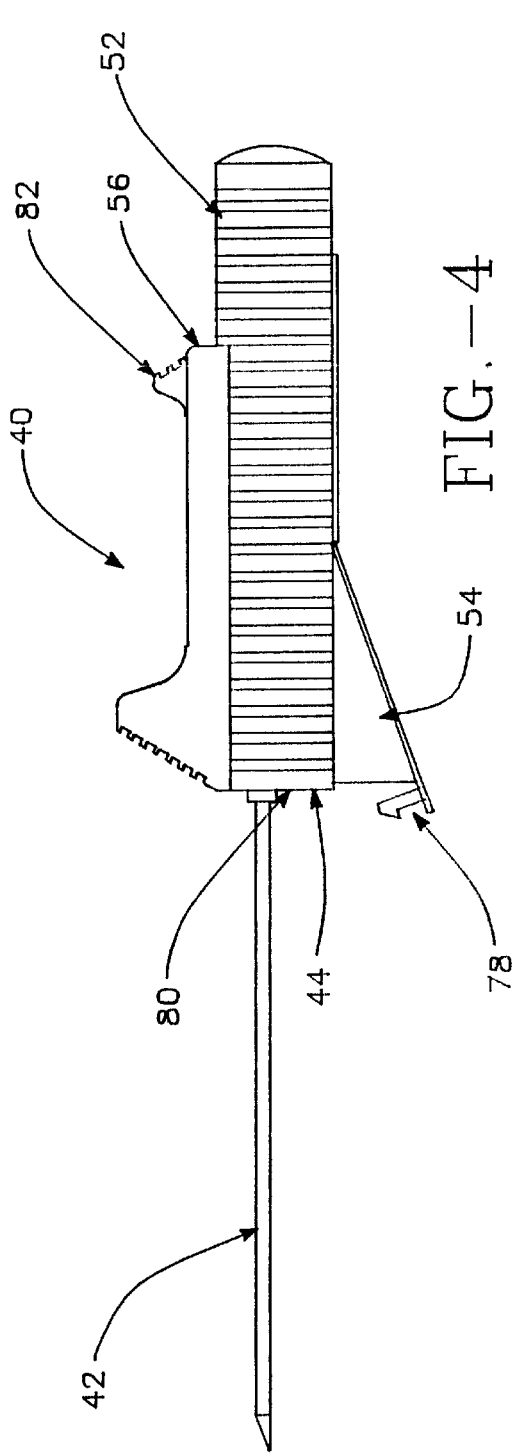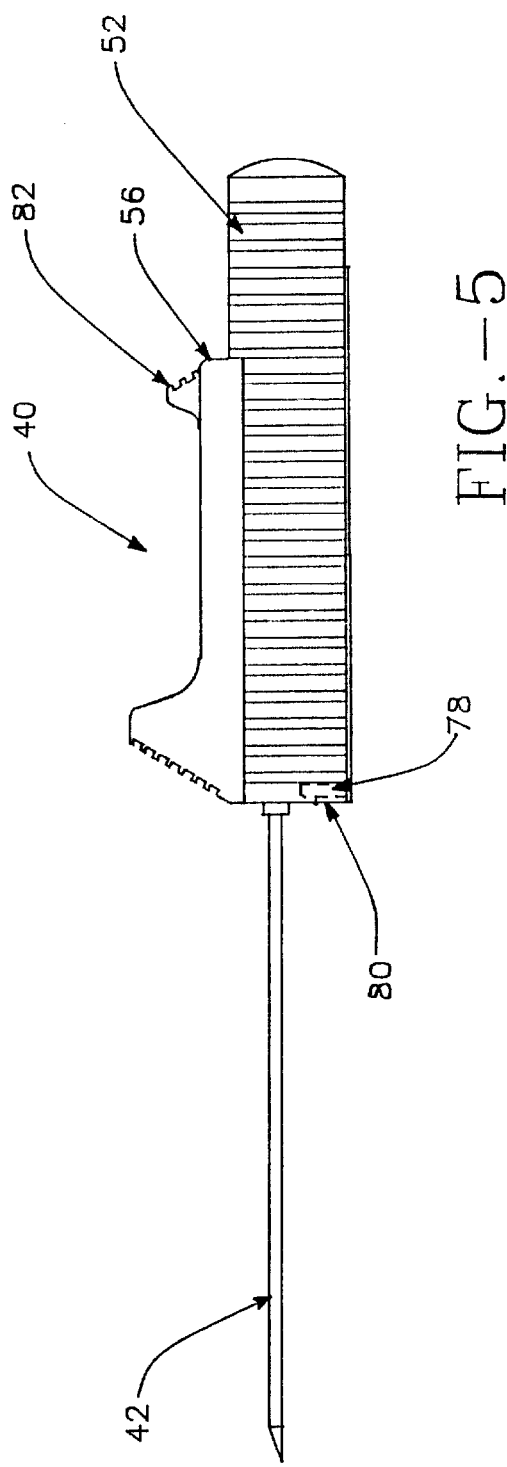

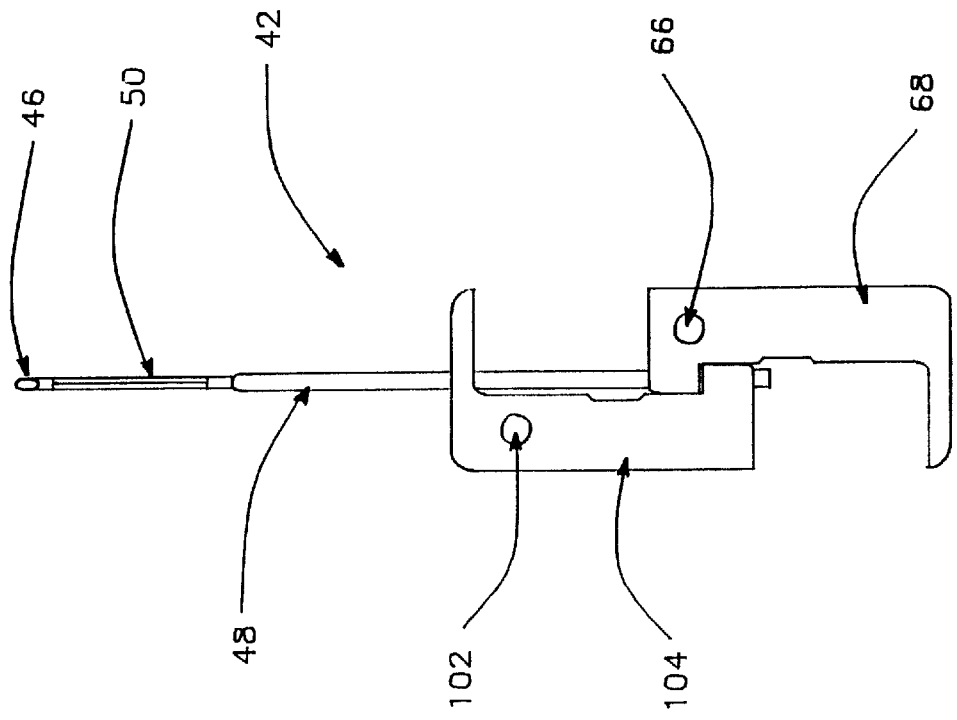
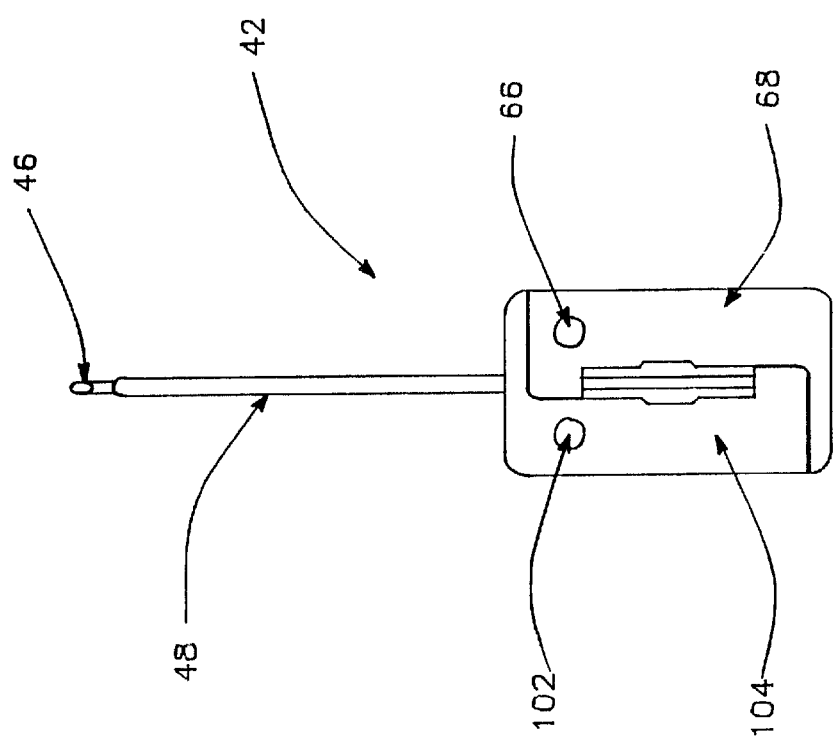

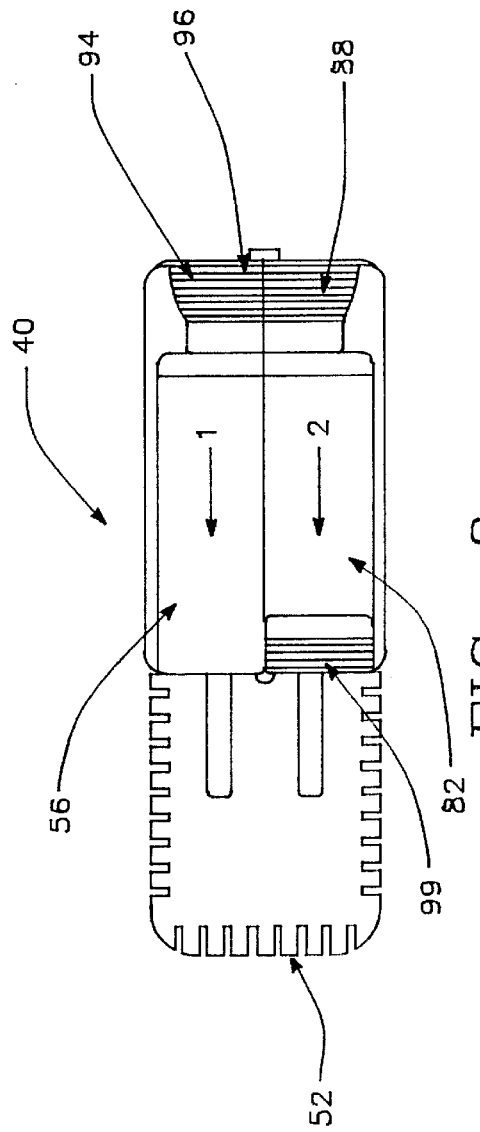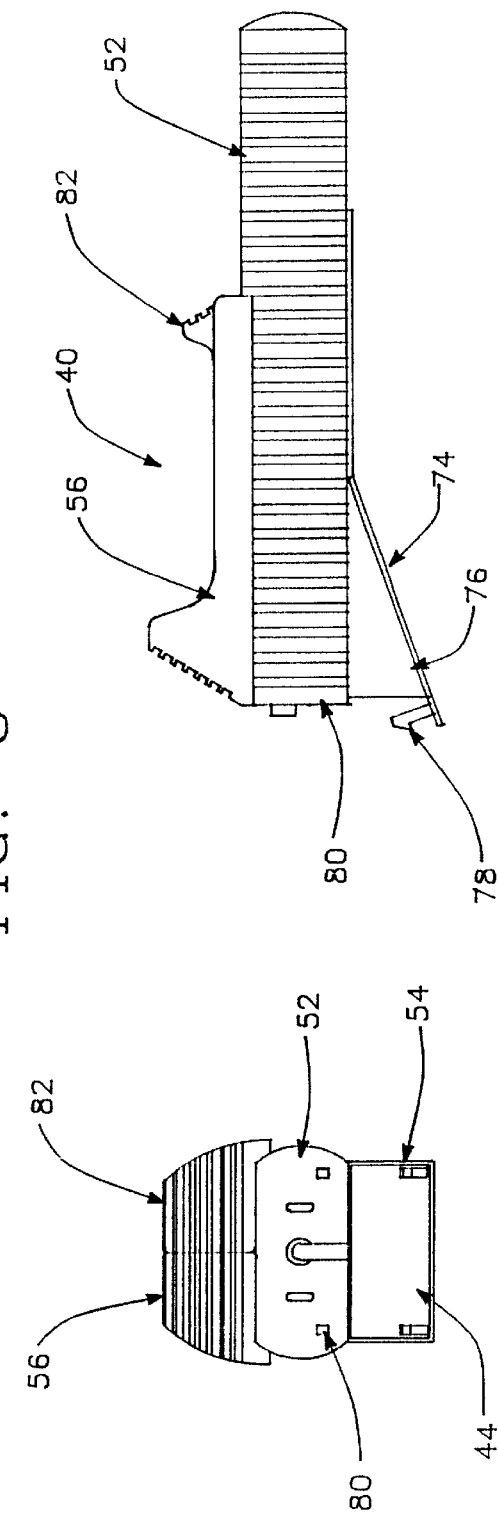

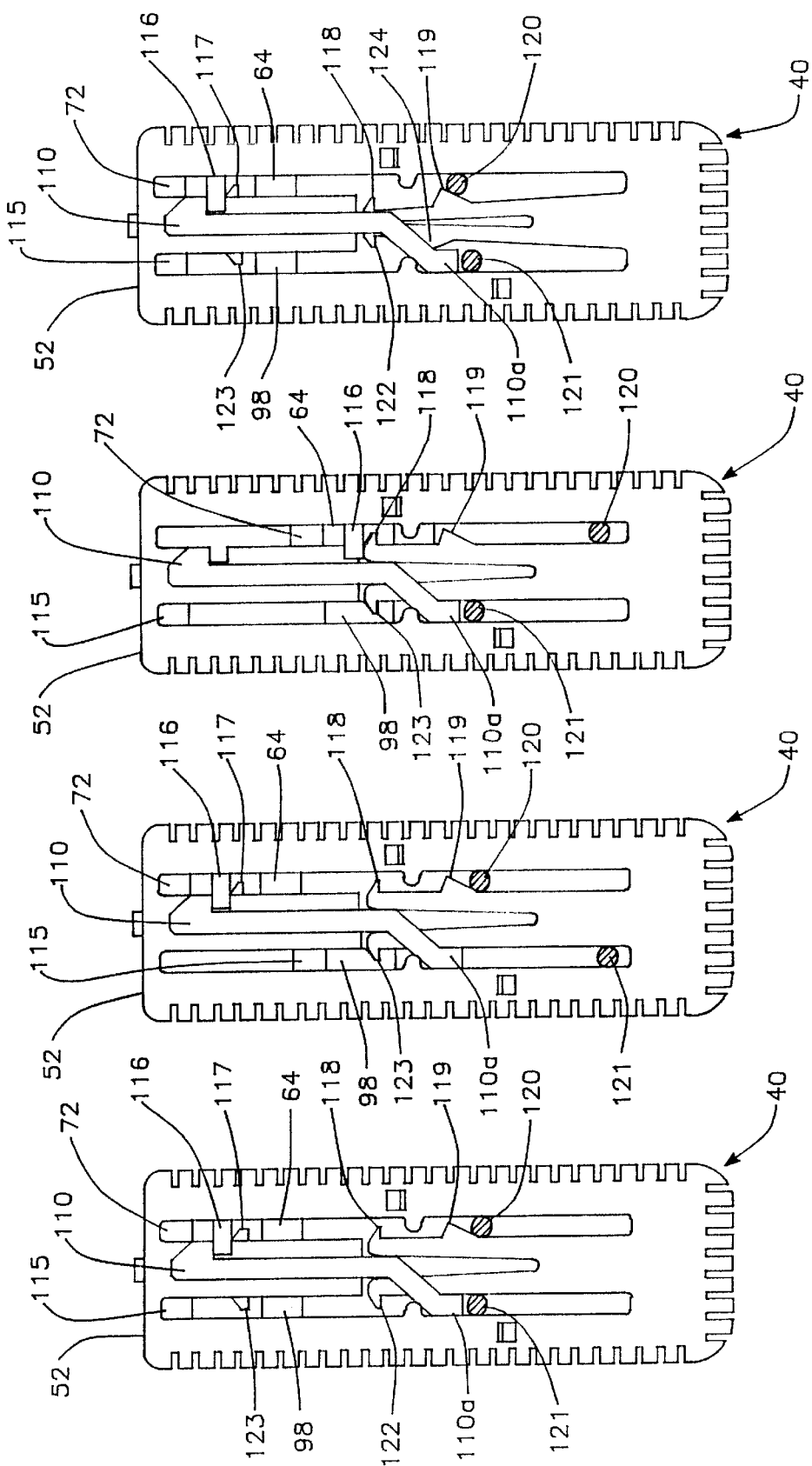

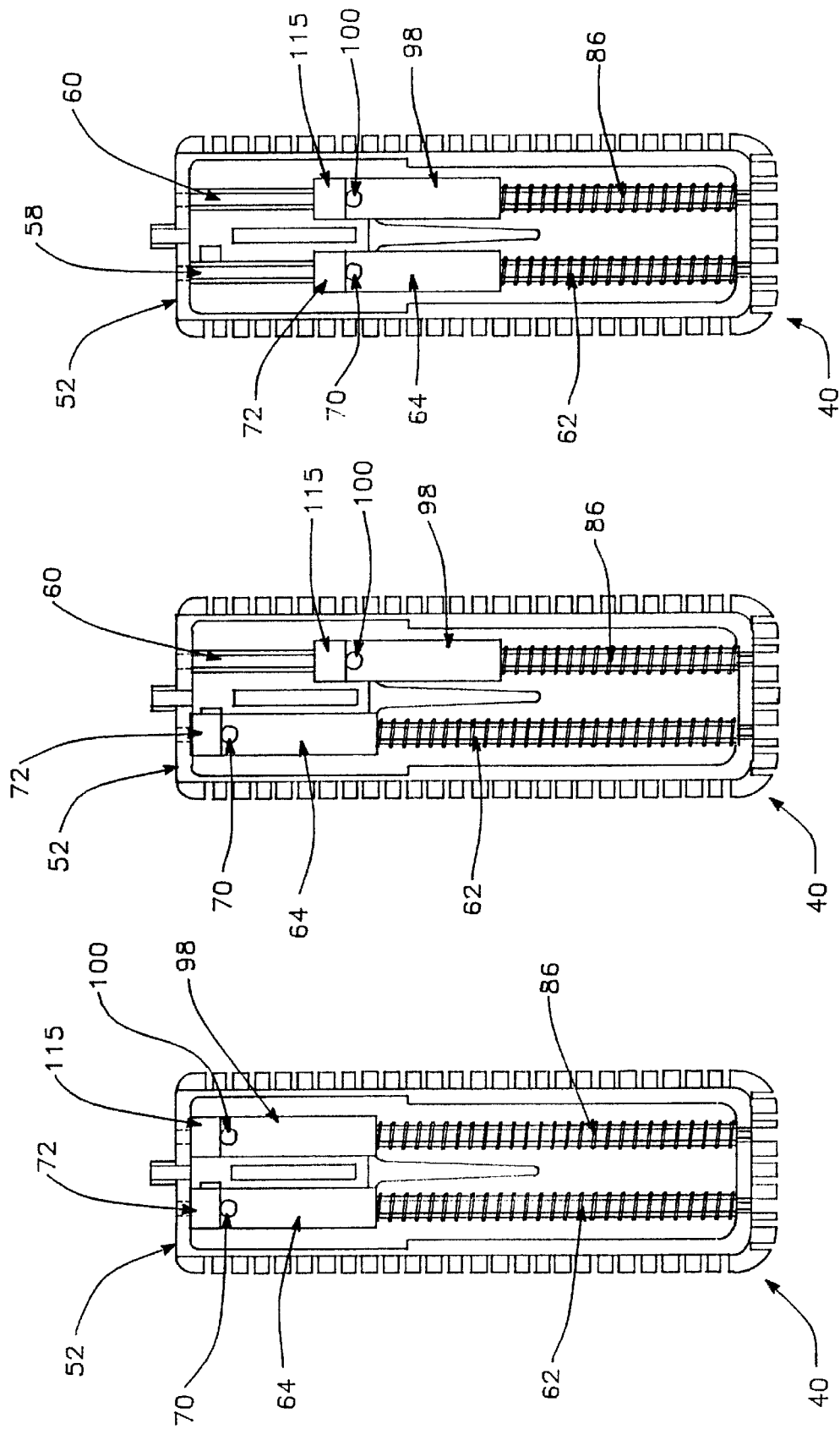

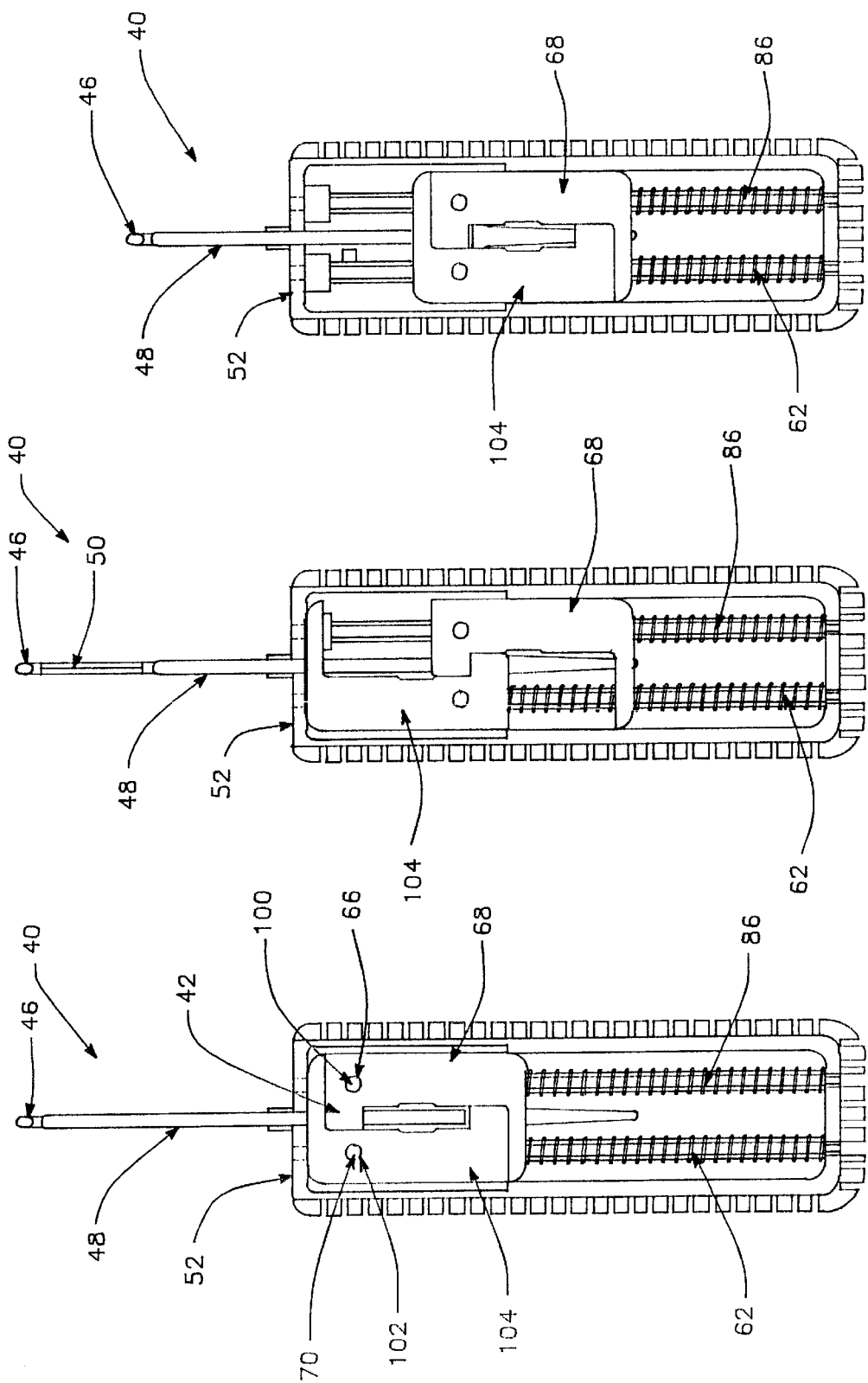

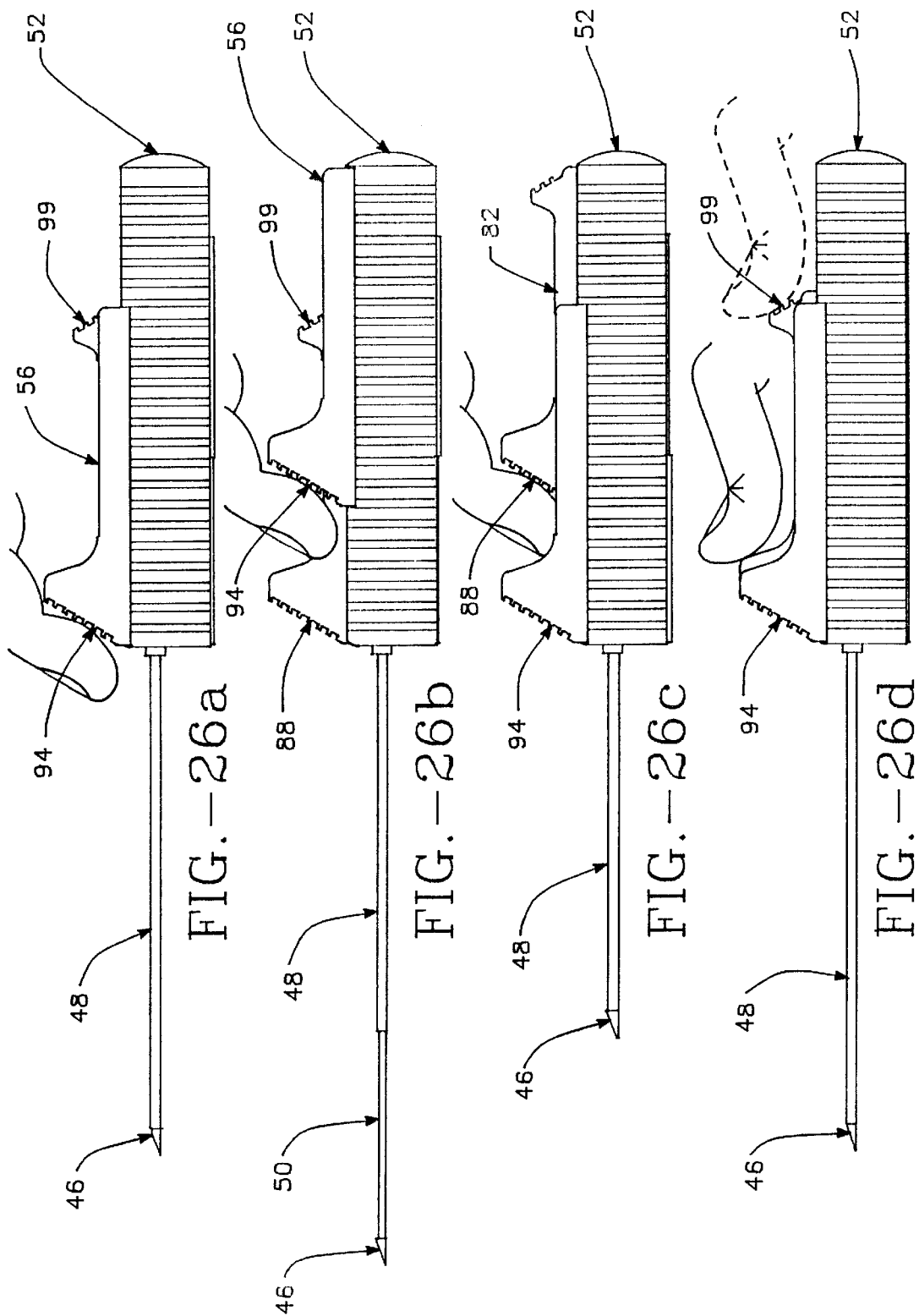

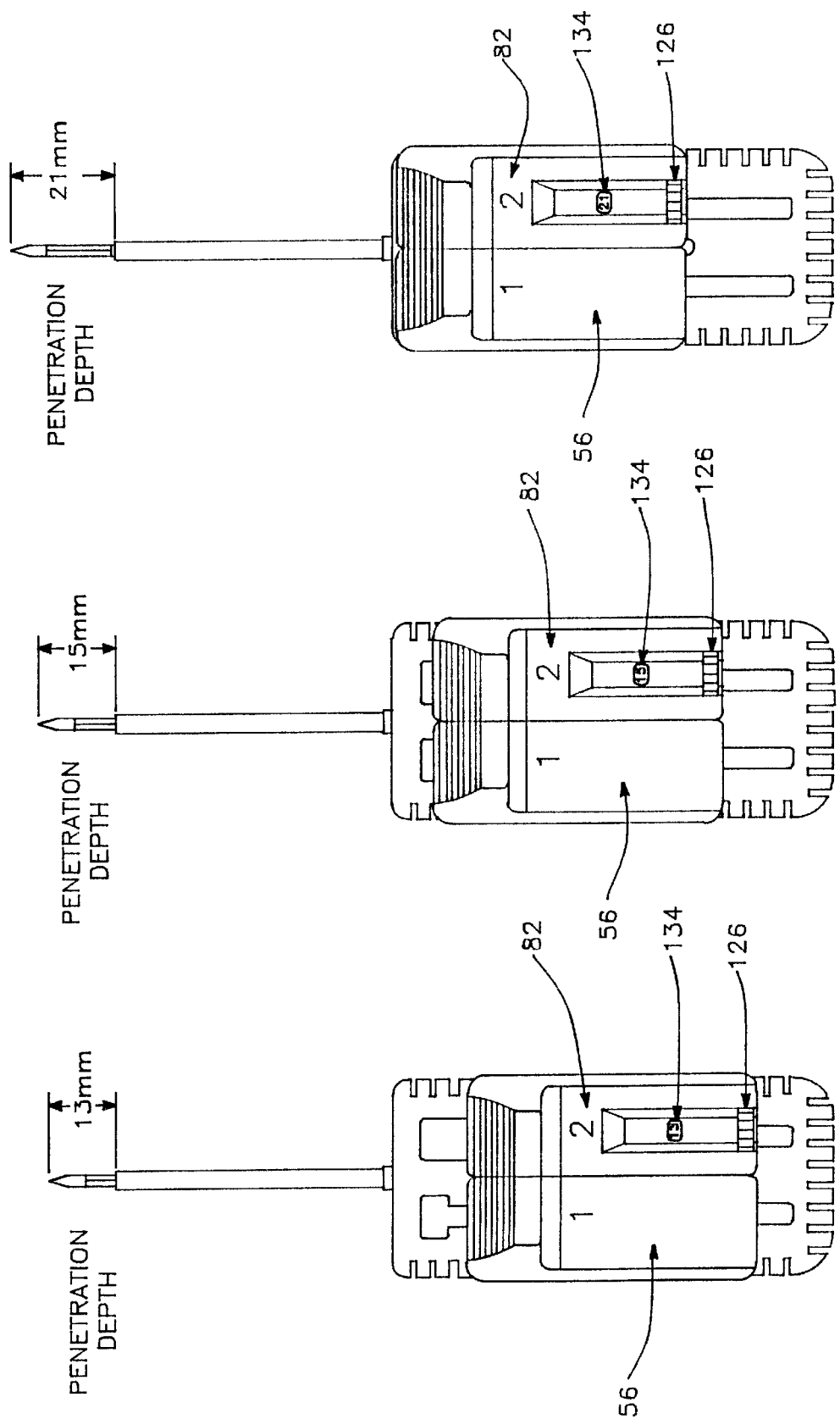

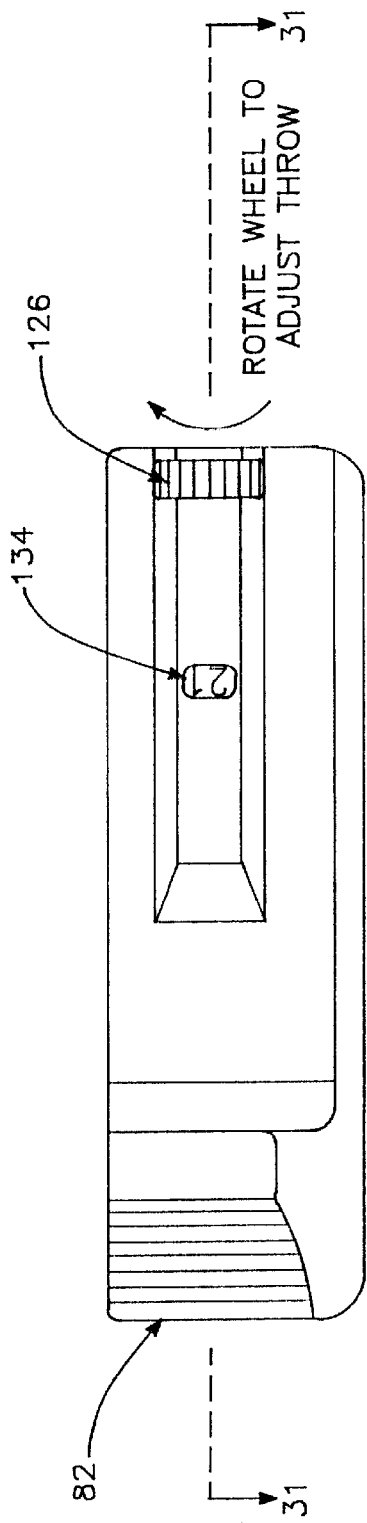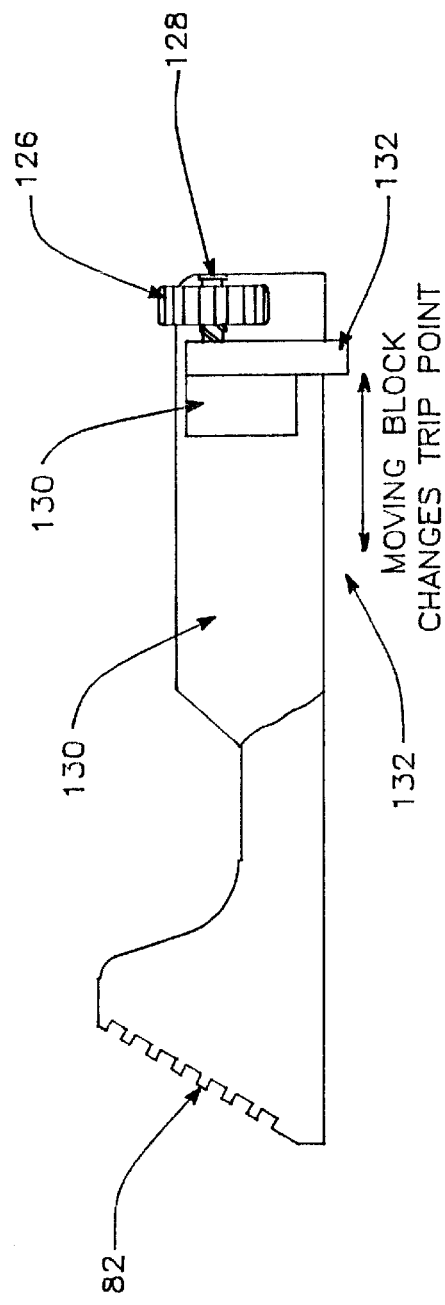

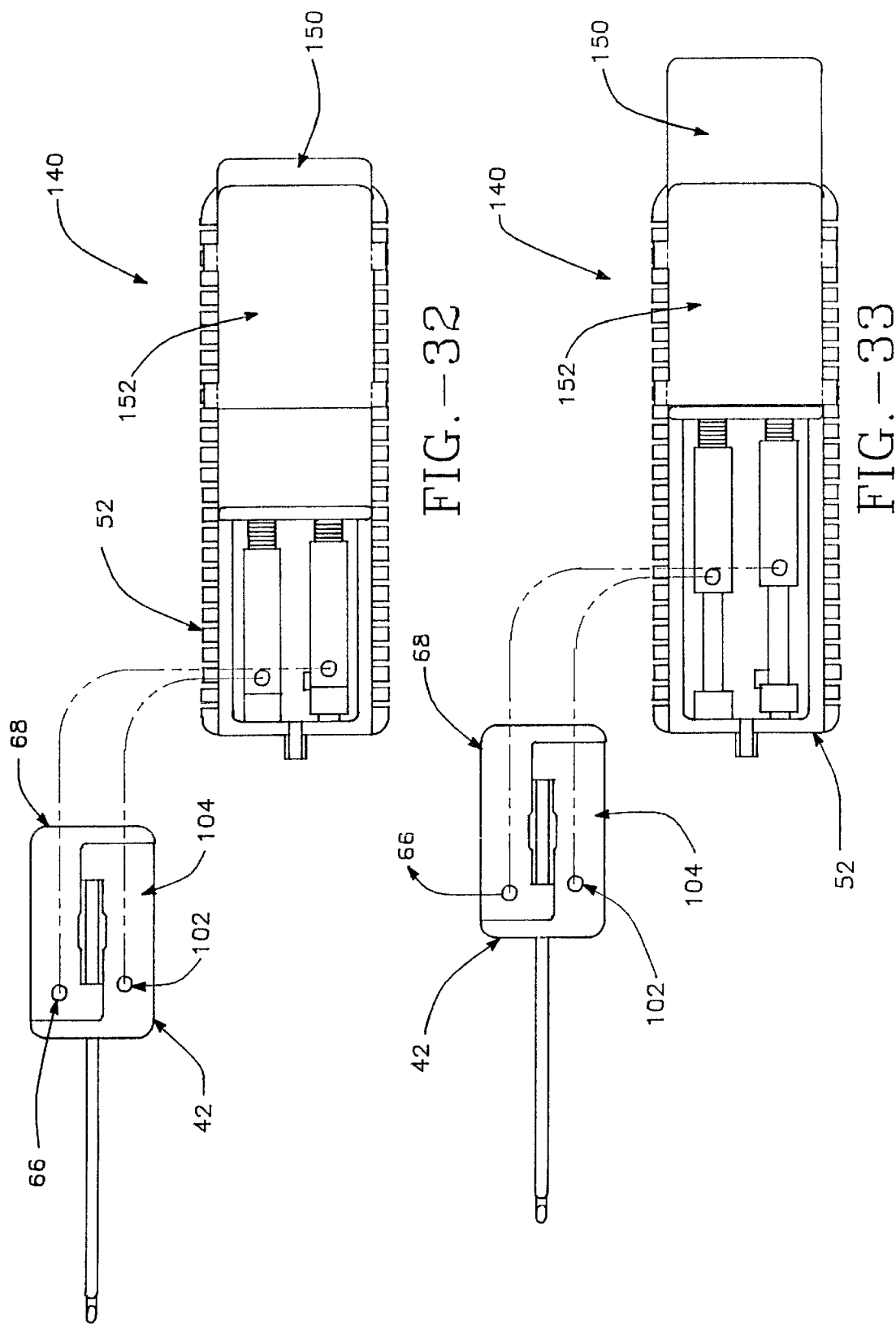

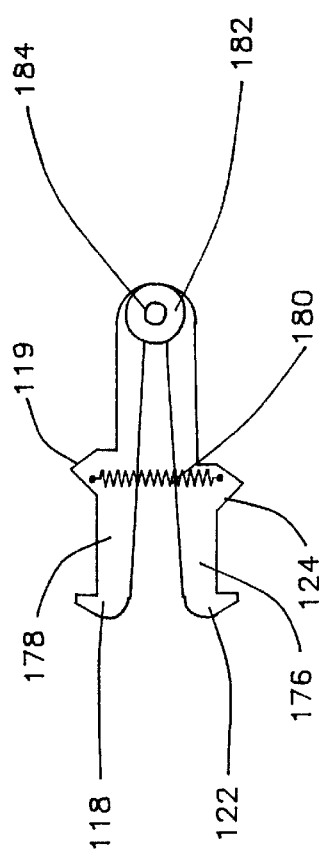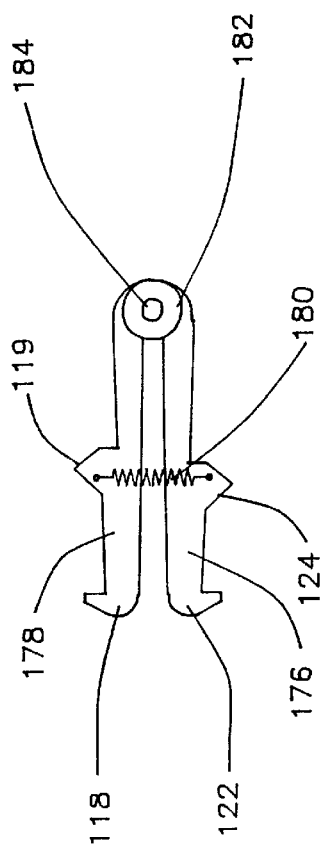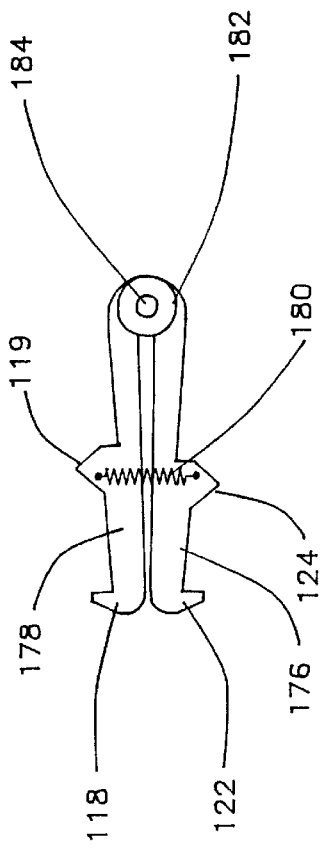

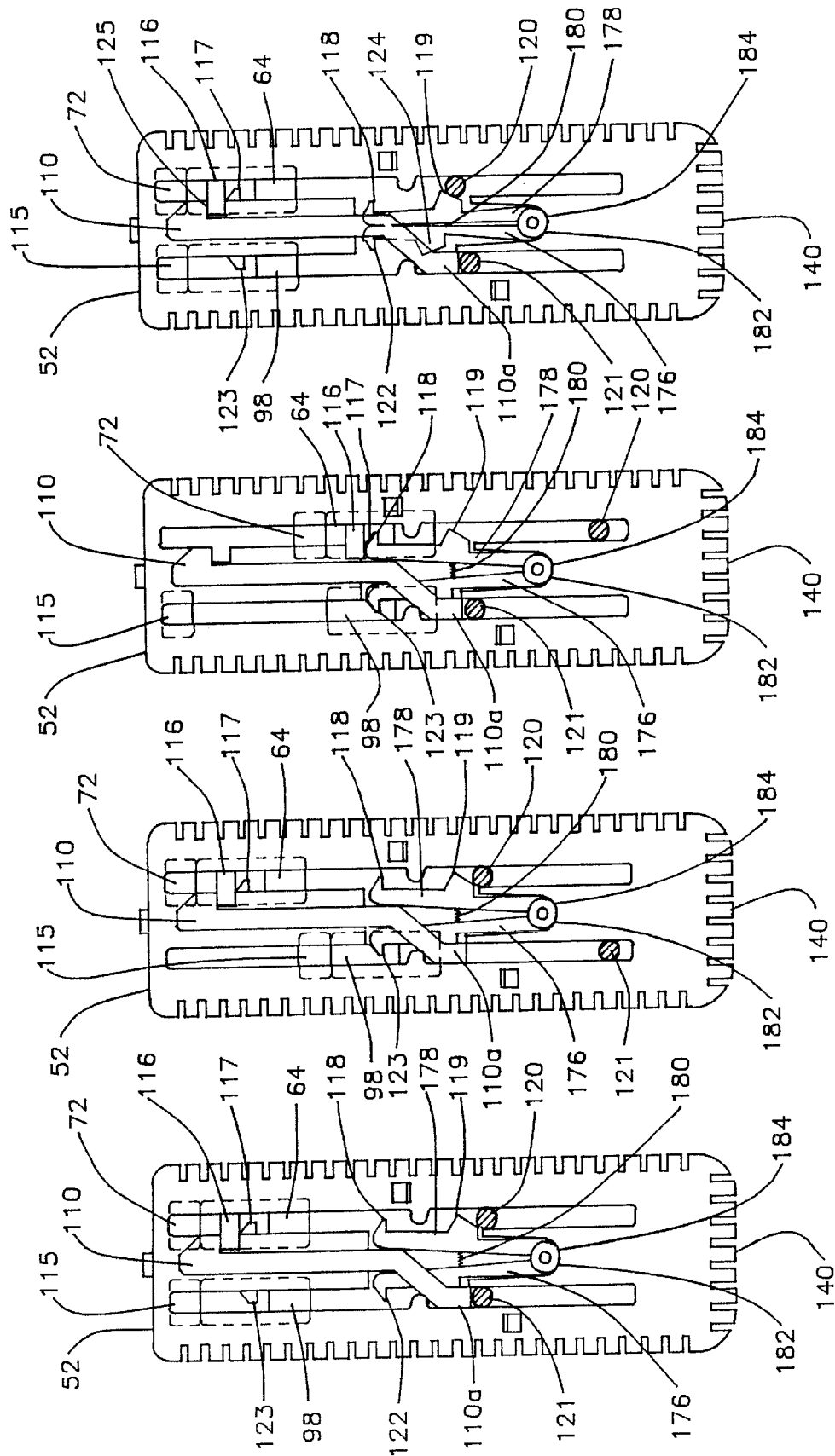

REUSABLE AUTOMATED BIOPSY NEEDLE HANDLE

The present application is a continuation-in-part of U.S. patent application Ser. No. 09/132,941, entitled, "Automated Biopsy Needle Handle", filed on Aug. 11, 1998, which is a continuation-in-part of U.S. patent application Ser. No. 09/076,181, entitled, "Biopsy Needle Handle", filed on May 12, 1998, both currently pending.

CROSS REFERENCE TO RELATED APPLICATIONS

The present application is related to the following United States Patent Application, which application is by the same inventor as the present invention, and which application is incorporated by reference herein in its entirety:

U.S. patent application Ser. No. 09/076,181, entitled, "Biopsy Needle Handle", filed on May 12, 1998, and currently pending.

FIELD OF THE INVENTION

This invention relates to a new handle design which provides the means to hold, operate and actuate a needle set to collect a tissue sample from humans or animals by a procedure referred to as tissue biopsy, and more particularly to an improved handle device which can be used in automated biopsy procedures to assist in the extraction of tissue in a precise manner.

BACKGROUND OF THE INVENTION

It is often desirable and frequently absolutely necessary to sample or test a portion of tissue from humans and even animals to aid in the diagnosis and treatment of patients with cancerous tumors, pre-malignant conditions and other diseases or disorders. Typically in the case of cancer or the suspicion of malignant tumors, a very important process called tissue biopsy is performed to establish whether cells are cancerous.

Biopsy may be done by an open or closed technique. Open biopsy removes the entire tissue mass or a part of the tissue mass. Closed biopsy on the other hand is usually performed with a needle-like instrument and may be either an aspiration (hollow needle on a syringe) or a core biopsy (special tissue cutting needle design). In needle aspiration biopsy, individual cells or clusters of cells are obtained for cytologic examination. In core biopsy, a segment of tissue is obtained for histologic examination which may be done as a frozen section or paraffin section.

The methods and procedures of obtaining tissue samples for cytologic or histologic examination have been performed historically by manual insertion and manipulation of the needle. These procedures are performed "blind" by the physician and guided by "feel" and known anatomic "landmarks".

Tumors are first noted in a patient by one of three ways, palpation, x-ray imaging or ultrasound imaging. Once a tumor is identified, a biopsy procedure is performed. Modern medical opinion dictates early detection of cancer, which increases the likelihood of successful treatment. Biopsy are performed on "Tumor Masses" as small as 2 millimeters in diameter. This procedure is performed under ultrasound or x-ray guidance. Tumors of this size cannot be biopsied reliably by hand since the tumor is about the same size as the biopsy needle. Manual attempts at biopsy can push the tumor away without piercing the mass. Automatic puncture devices are needed to accelerate the needle at such a velocity that even a small tumor can be pierced.

Two very important innovations in the field of medical technology have influenced the field of tissue biopsy in the last five years.

One, the use of tissue imaging devices which allow the physician to "see" inside the body and visually guide the needle to the tumor mass.

Two, the invention of the Automatic Core Biopsy Device (ACBD) or "Biopsy Gun". The ACBD is an instrument which propels a needle set with considerable force and speed to pierce the tumor mass and collect the tissue sample. This ACBD device has allowed physicians to test tissue masses in the early stages of growth and has contributed to the medical trend of early diagnosis and successful treatment of cancer.

Examples of such ACBD devices have been described with respect to the collection of tissue samples in U.S. Pat. Nos. 4,651,752, 4,702,260, and 4,243,048.

Historically, Automated Core Biopsy Devices (ACBD) have used the "Tru-Cut" needle set design. The "Tru-Cut" needle is comprised of an inner notched stylet with an outer cannula. The stylet is a needle with a notched cut out at the distal end. The cannula is a hollow needle with an angled cutting surface at the distal end which slides over the stylet. When the stylet is advanced into tissue under spring powered force, the tissue is pierced and relaxes into the notched cut out. When the cannula is slid forward, the tissue in the notch of the stylet is sliced off and retained in the notch until the cannula is drawn back. The "Tru-Cut" needle yields a core sample which is semi-circular in cross section, with length of the core sample determined by the stroke of the ACBD.

Subsequent improvements to the "Tru-Cut" needle design have been introduced and are described in U.S. Pat. No. 5,449,001.

There are numerous prior art devices on the market that employ this process. However, in prior art designs, if the physician requires a lightweight and simplistic biopsy device which utilizes single-handed automated deployment of the entire needle set for precision and simplicity, a problem is presented.

Furthermore, if the physician requires a biopsy device which cycles the needle set a short or longer distance into the tissue mass, a separate device for each needle distance desired has to be purchased. Current prior art devices have captive needle sets which require the physician to have many different styles of devices available to perform the range of procedures that are encountered in a biopsy procedure. This is a design limitation because it creates a situation of compromise between the physician's desire to use the optimum needle for a given procedure and the need to overstock all the possible combinations of needle gauges, lengths and predetermined extensions of the stylet that are available for a biopsy procedure. Furthermore, in the era of managed health care, the cost of biopsy procedures has come under scrutiny. The disposable single use devices are expensive and not desirable due to their high single use cost. Thus, prior art designs of the ACBD have a need for a design that allows the interchangeability of the needle sets to accommodate the parameters of the biopsy procedure to be performed.

On the other hand, the physician may use a prior art device that is capable of functioning automatically or at different distance settings to perform a range of biopsy procedures. However, such an automatic adjustable device is mechanically complicated and requires external settings to be made to allow the mechanism to perform. Also the reusable handles have, in prior art, been costly to obtain because of the expense of manufacturing a complicated mechanical design. Since the mechanism of the prior art ACBD is designed to have a stylet that moves forward first and then activates the cannula, thus advancing the needles in their proper sequence, these prior art devices require many high tolerance mechanical moving parts with precision bushings in order to have the device operate properly. The required repeated use of the reusable design dictates that the mechanical design be robust and operate many cycles without undue wear or failure. These requirements have produced in prior art, ACBDs that are heavy, large and costly due to their complicated mechanical designs.

Thus, the size, weight and expense of single use and reusable prior art ACBD's have limited their use. An improved design is needed that gives the physician an automatic, small, light weight, easy to single-handedly operate and cost effective design that improves the function of obtaining a tissue sample.

SUMMARY OF THE INVENTION

It is therefore an advantage of the present invention to provide a handle assembly for a needle set which automatically captures and allows the removal of a tissue sample from a tissue mass for examination in one operation.

It is another advantage of the present invention to provide a handle assembly which can reliably obtain biopsy samples, is simple in design, easy to use and cost effective.

It is a further advantage of the present invention to provide a handle assembly for a needle set with a mechanism to single handedly operate the cocking of each stage and the subsequent firing of both stages with out repositioning the hand.

It is another advantage of the present invention to provide a handle assembly which allows the user to obtain a tissue sample of a predetermined size.

It is yet another advantage of the present invention to provide a handle assembly which allows the user to choose the parameters of the needle set to be used to obtain the optimal tissue samples for any given biopsy procedure.

It is a further advantage of this invention to provide a handle assembly for a needle set with spring powered stages to actuate the stylet and cannula to assist in severing the tissue from the surrounding biopsy site.

It is another advantage of the present invention to provide a handle assembly for a needle set which incorporates a safety feature therein to prevent accidental firing.

It is yet a further advantage of this invention to provide a handle assembly for a needle set which allows the single handed operation of locking the spring powered stages for the cannula and stylet.

It is another advantage of the present invention to provide a handle assembly for a needle set which provides the firing mechanism in the same component that cocks the spring loaded coupling.

It is yet a further advantage of this invention to provide a handle assembly for a needle set which incorporates the cocking of the cannula and stylet, the safety feature and the firing mechanism in a single assembly, thus allowing real single-handed operation without the need of separate components, buttons or slides to activate each of these actions.

It is a further advantage of this invention to provide a handle assembly for a needle set that is disposable and can be delivered sterilized prior to the procedure.

It is another object of this invention to provide a handle assembly for a needle set which can be used to obtain multiple tissue samples from the same biopsy site.

It is yet another advantage of this invention to provide a handle assembly which is metal and entirely automatic.

These and other advantages of the invention will be apparent from the following descriptions and claims.

In accordance with the present invention and new and improved automated biopsy handle assembly for a needle set is provided. The handle assembly has an opening that allows for the insertion of a needle set. The needle set consists of an outer hollow cannula and an inner pointed tip stylet.

The handle assembly includes a housing, a locking lid, a cannula extension and a stylet extension. The housing is rectangular in shape and has a hollow inside. The cannula extension and the stylet extension are slidably attached to the top of the housing, and the locking lid extends from the bottom of the housing, with the inner mechanisms shielded therebetween. Inside the housing are two cylindrical rods which guide the stylet and cannula when a biopsy is performed and a tissue sample retrieved. The rod which guides the cannula has mounted thereon a spring and a cannula coupling for securing the cannula in the housing. The cannula includes an aperture in its base for connecting to a protrusion on the cannula coupling. The cannula coupling is pushed against the spring by a cannula pushing member, which is attached to the cannula extension, until it reaches a position wherein the cannula is spring loaded and ready for release.

Similarly, the rod which guides the stylet has mounted thereon a spring and a stylet coupling for securing the stylet in the housing. The stylet includes an aperture in its base for connecting to a protrusion on the stylet coupling. The stylet coupling is pushed against the spring by a stylet pushing member, which is attached to the stylet extension, until it reaches a position wherein the stylet is spring loaded and ready for release. Once the stylet is released, the spring urges the stylet forward in a rapid motion piercing the tissue. The cannula is then automatically released wherein the spring urges the cannula forward in a rapid motion severing the prolapsed tissue which resides in the notch of the stylet.

The locking lid covers the bottom of the housing and has a descending portion having side walls which provides the opening for insertion of the needle set. The front of the locking lid includes a catch on each side which engages a cut-out located on the front side of the housing. Once the needle set is inserted, the descending portion is pushed up to be flush with the bottom of the housing and the needle set is secured inside the housing by engagement of the catch and cutout on each side of the front of the housing. The locking lid ensures one patient use of the biopsy needle set and housing.

In a second embodiment wherein the handle assembly is comprised of metal, the lid is a slidable lid. The slidable lid allows for insertion of the needle set in pre-cocked and cocked positions. The housing includes a fixed cover on the bottom of the housing and the slidable lid located within the housing parallel to the fixed cover. The slidable lid is inserted into a slot which is located within the housing in the bottom portion. The fixed cover extends over approximately a one-third portion of the bottom of the back of the housing, thereby leaving an opening for insertion of the needle set when the slidable lid is in an open position.

The slidable lid includes a notch located on one side at a front end of the slidable lid for locking the lid into the closed position after insertion of the needle set. The notch is engaged by a pivoting locking member located in a cavity in a side of the housing near a front end of the housing. The pivoting locking member pivots about a pivot bar which extends through the cavity in the housing A locking spring, located in a bore in the cavity, rests on a bottom portion of the pivoting locking member. The locking spring provides a biasing force against the bottom portion of the pivoting locking member causing the top portion of the pivoting locking member to engage the notch when the slidable lid reaches the appropriate place on the housing. To release the slidable lid from the pivoting locking member, the user pushes in on the bottom portion causing the top portion to move outward from the notch. The slidable lid also includes a lip member for moving the slidable lid between the open and closed positions.

The cannula extension and the stylet extension cover the top of the housing. Alternatively, the extensions may be called actuators. The extensions advantageously adapt the handle to one-hand operation by the user. The stylet extension also includes a protrusion. The stylet extension, together with the protrusion are pushed forward, until the protrusion interacts with a locking member protrusion to release the stylet. The stylet coupling then moves forward releasing the cannula side of the mechanism which will be explained later.

At the front of each slidable extension, a pushing portion is provided. The pushing portions include ribs for enhanced friction between the user's thumb and the pushing portion during the biopsy procedure. The stylet extension also includes a pushing portion on the back end for actuating the stylet. Located inside, behind the stylet extension near the front of the housing is a stylet coupling for engaging the stylet in the housing. The stylet coupling includes a protrusion which is inserted into an aperture located on the base of the stylet. Similarly, located inside, behind the cannula extension near the front of the housing is a cannula coupling for engaging the cannula in the housing. The cannula coupling includes a protrusion which is inserted into an aperture located on the base of the cannula.

In operation, the needle set, including the stylet and cannula, are inserted into the handle assembly in the descending portion of the locking lid, which is then pushed upward and secured via the catch and the cut-out located on the front of the locking lid and the housing, respectively. The cannula extension is moved rearward, with a single user's hand, until the cannula is in the spring loaded position and the first locking member has engaged the second locking member. A return spring under the cannula extension returns it to its original position after the first locking member is engaged. The stylet extension is then moved rearward, with a single user's hand, until the stylet is in the spring loaded position and the first locking member has engaged the second locking member. A bias spring under the extension maintains the extension in the rearward position after the second locking member is engaged. With the same single user's hand, the stylet and the cannula are inserted into the patient near the biopsy area. The stylet is then urged forward against the bias spring by pushing the stylet extension forward with the user's thumb. This bias spring keeps the stylet extension in the rearward position and prevents accidental firing until the operator pushes the stylet extension forward. The stylet is released and fired forward thereby automatically releasing the cannula. The tissue is severed and captured in the notch of the stylet. After removing the needle set from the biopsy site, the cannula is pressed back using the cannula extension so that the tissue sample is exposed and may be removed. The stylet is then pulled back into the starting position. Moving the stylet extension rearward again reestablishes the stylet and the cannula in relation to each other in order to allow subsequent reinsertions into the biopsy area for additional tissue samples. Accordingly, the inventive biopsy handle allows the user the ability to take multiple tissue samples conveniently and quickly using only a single hand.

BRIEF DESCRIPTION OF THE FIGURES

The above and other advantages of the present invention will be apparent upon consideration of the following detailed description, taken in conjunction with the accompanying drawings, in which like reference characters refer to like parts throughout, and in which:

FIGS. 1–5 are side views of an embodiment of the handle assembly of the present invention showing insertion and securing of the needle set into the locking lid and housing according to the present invention;

FIGS. 6–7 are top views of a needle set;

FIG. 8 is a top view of an embodiment illustrating a cannula and a stylet slidable extension attached to a housing according to the present invention;

FIG. 9 is a side view of an embodiment of the handle assembly showing the housing, the cannula and the stylet slidable extensions and a locking lid according to the present invention;

FIG. 10 is a front view of an embodiment of the handle assembly showing the locking lid extended in an open position according to the present invention;

FIGS. 15–18 are top views showing an embodiment of the inner mechanisms of the slidable extensions and the housing at various stages of cocking and releasing the cannula and stylet couplings according to the present invention;

FIGS. 19–21 are inside bottom views of an embodiment of the housing at various stages of cocking the cannula and stylet couplings sequentially according to the present invention;

FIGS. 22–24 are inside bottom views of an embodiment of the housing having a needle set at various stages of sequentially cocking the attached needle set according to the present invention;

FIGS. 25a–e and 26a–d are side views of an embodiment of the handle assembly having a needle set illustrating the sequencing of the extensions and the sequence of needle set action in retrieving a tissue sample according to the present invention;

FIGS. 27–29 are top views showing of an embodiment of a housing assembly showing the extension having an adjustable wheel wherein the stylet needle is extended to various predetermined lengths;

FIG. 30 is a top view of an embodiment of the slidable extension of the handle assembly illustrating the numeric indicator and the window according to the present invention;

FIG. 31 is a broken away view of an embodiment of the slidable extension of the handle assembly through lines 30—30 of FIG. 30 according to the present invention;

FIG. 32 is a bottom view of another embodiment of the handle assembly showing a slidable lid open for insertion of the needle set in a pre-cocked position according to the present invention;

FIG. 33 is a bottom view of the embodiment of the handle assembly of FIG. 32 showing the slidable lid open for insertion of the needle set in a cocked position according to the present invention;

FIG. 41–43 are a top views of the embodiment of the handle assembly of FIG. 32 showing the details of the spring-loaded cannula and stylet hook assembly at various stages during the biopsy procedure according to the present invention; and FIG. 44–47 are top views showing the inner mechanisms of the housing assembly at various stages of cocking and releasing the cannula and stylet couplings of the embodiment of FIG. 32 according to the present invention.

DETAILED DESCRIPTION OF THE PREFERRED EMBODIMENT

Figure 11:
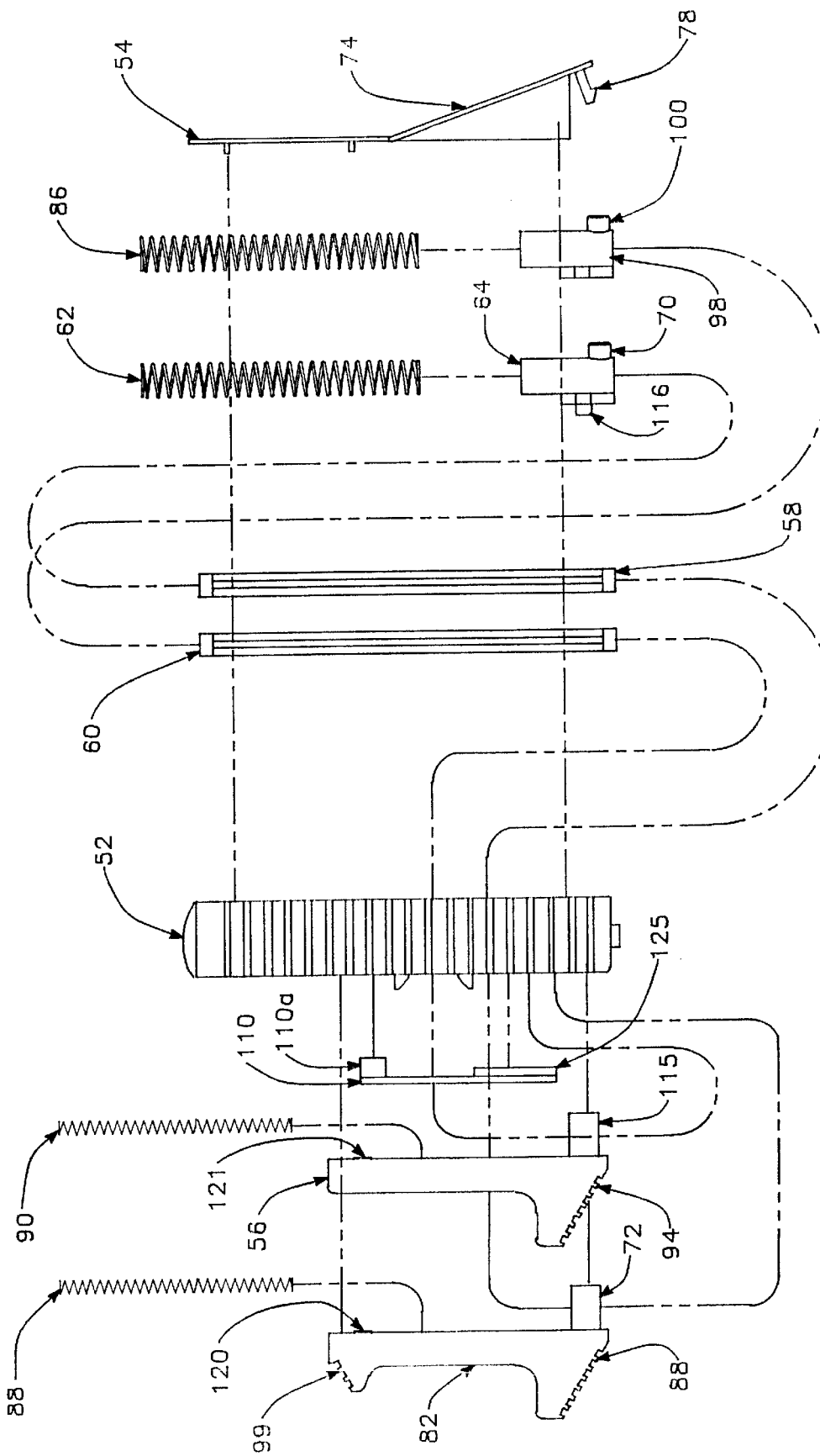
FIG. 11 is an exploded side view of an embodiment of the handle assembly according to the present invention.

First Embodiment:

The present invention will now be described with reference to FIG. 1 through 47 which in general relate to a novel handle assembly which can be used in an automated biopsy procedure to assist in the extraction of tissue in a precise manner using only one of a user's hands. It is understood that the principles of the present invention may be suitable for a variety of functions and incorporated into various biopsy devices.

Referring now to FIGS. 1 through 7, there is shown a handle assembly 40 and a needle set 42. The handle assembly 40 has an opening 44 that allows for the insertion of the needle set 42 as will be explained hereinafter. The needle set 42 (which is not part of this invention) is an integral unit and consists of an inner pointed tip stylet 46 and an outer hollow cannula 48, as shown in FIGS. 6 and 7. The stylet 46 and the cannula 48 are capable of being urged forward separately into the biopsy area in a defined motion in relation to each other. The stylet 46 includes a notch 50 which is ground at the distal end of the needle and is a repository for the tissue that is pierced by a forward motion of the needle. The secondary motion of the cannula 48 coaxially over the stylet 46 cuts and captures the tissue in the notch 50 of the needle, thus allowing the tissue to be removed from the biopsy area and examined outside the patient.

With reference to FIGS. 8 through 11, the handle assembly 40 will now be described. The handle assembly 40 includes a housing 52, a locking lid 54, a cannula extension 56 and a stylet extension 82. The housing 52 is rectangular in shape and has a hollow inside. The cannula extension 56 and the stylet extension 82 are slidably attached to the top of the housing 52 by protrusions 120 and 121, respectively, and are single hand-operated extensions. Alternatively, the extensions may also be called actuators. The locking lid 54 is attached to the bottom of the housing 52. The extensions and the locking lid shield the inner mechanisms of the handle assembly, as will be explained hereinafter. The preferred material for the handle assembly 40 is a lightweight plastic although it is understood that the handle assembly may be formed with metals, polymers and other materials. Moreover, the handle assembly may be disposable and delivered sterilized prior to the biopsy procedure or not.

Figures 12, 13, 14:
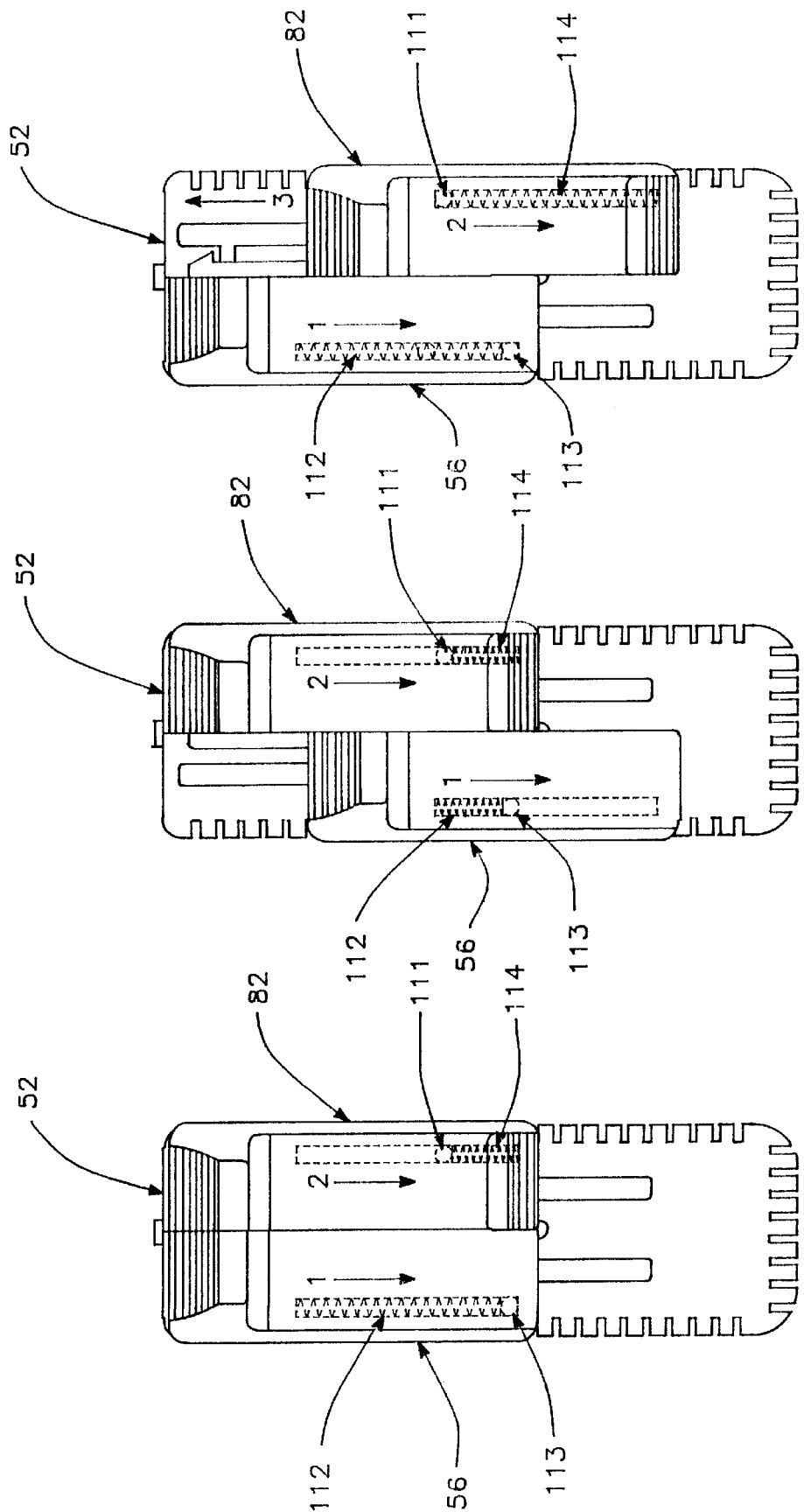
FIG. 12 is a top view of an embodiment of a housing assembly showing the two extensions and the return springs under the extensions according to the present invention.
FIG. 13 is a top view of an embodiment of the housing assembly showing the cocking of the cannula extension according to the present invention.
FIG. 14 is a top view of an embodiment of the housing assembly showing the cocking of the stylet extension according to the present invention.
Figure 25A:
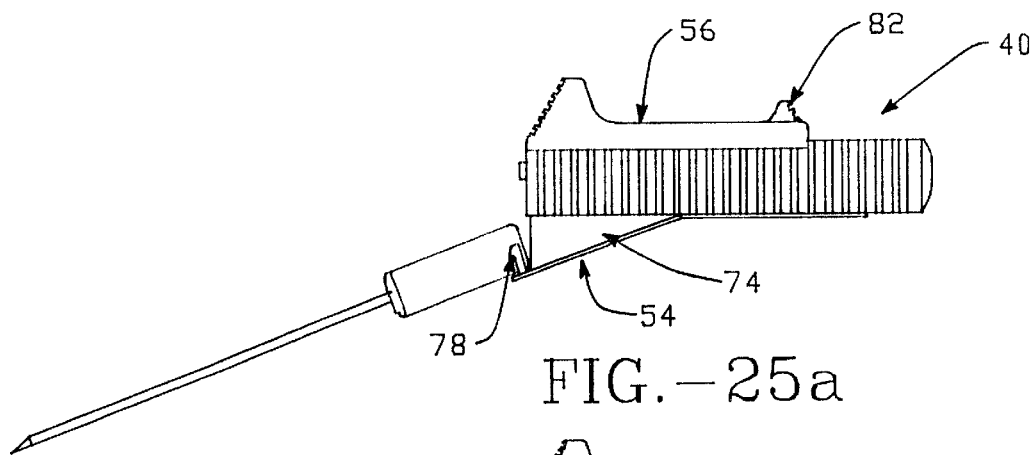
Figure 25B:
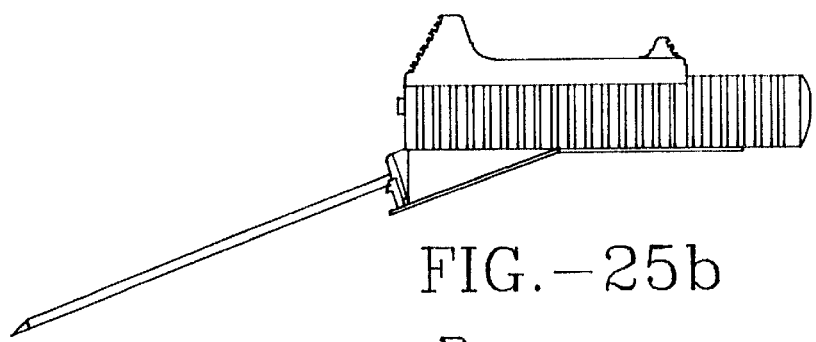
Figure 25C:
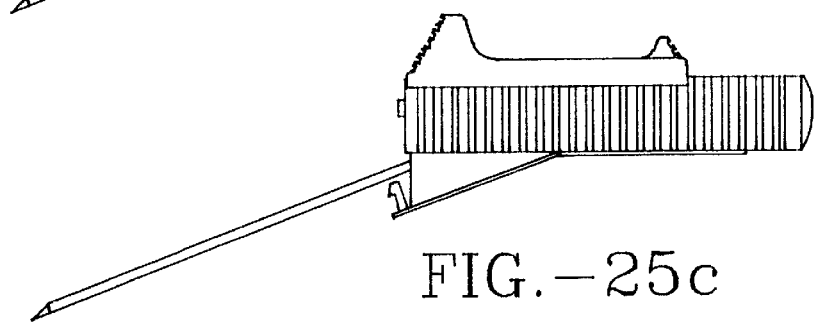
Figure 25D:
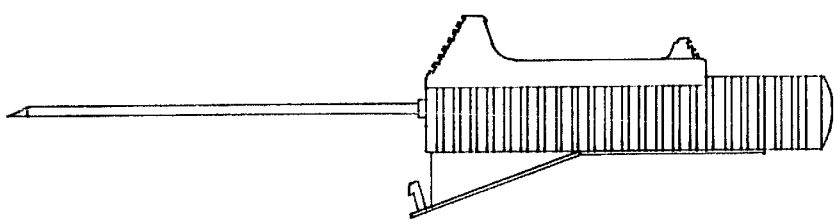
Figure 25E:
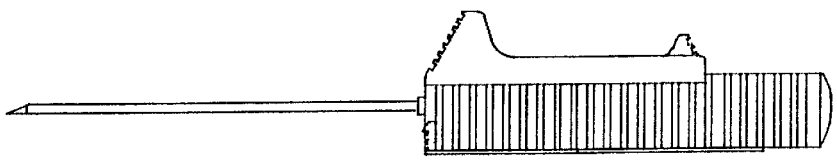
Figure 34:
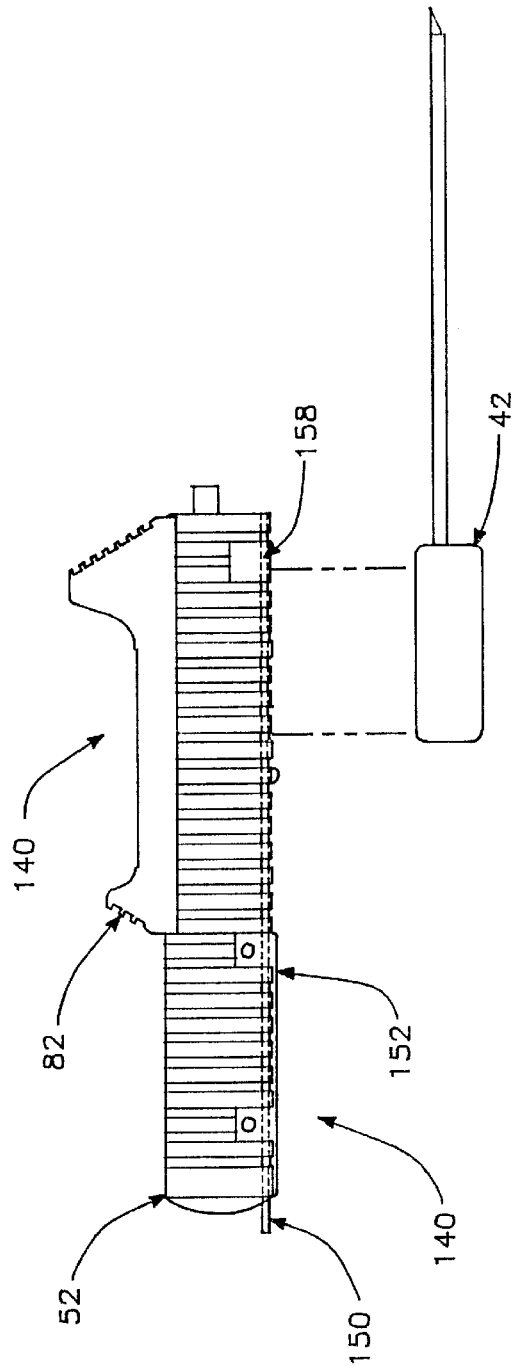
FIG. 34 is a side view of the embodiment of the handle assembly showing a slidable lid open for insertion of the needle set in a pre-cocked position corresponding to FIG. 32 according to the present invention.
Figure 35:
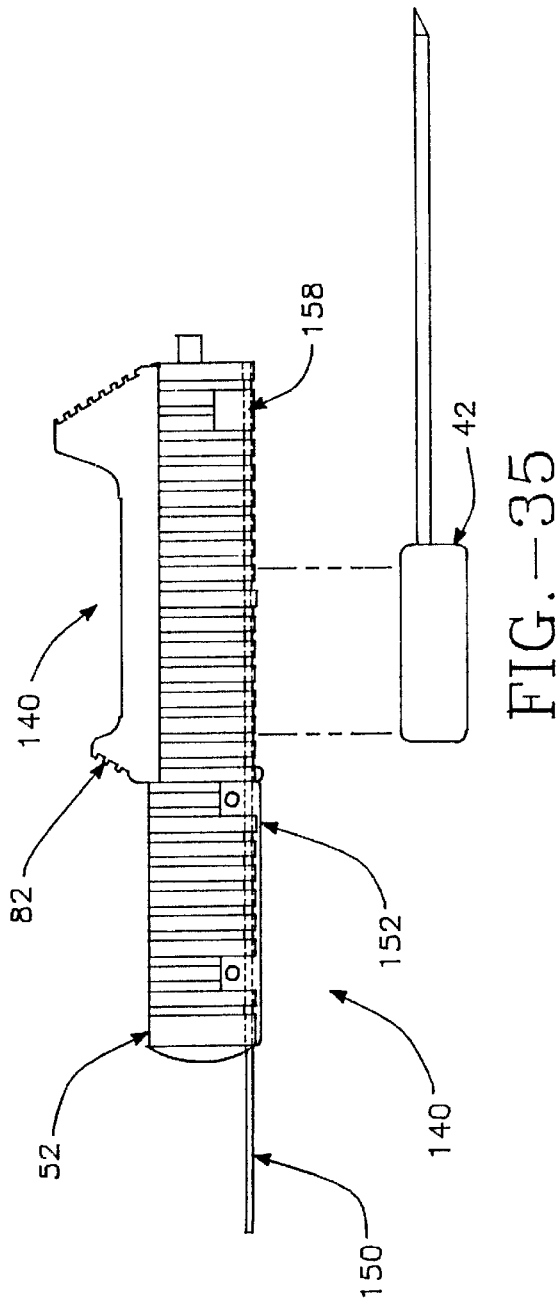
FIG. 35 is a side view of the embodiment of the handle assembly showing the slidable lid open for insertion of the needle set in a cocked position corresponding to FIG. 33 according to the present invention.

Inside the housing 52 are two cylindrical rods 58, 60 (FIG. 21) which guide the stylet and cannula when a biopsy is performed and a tissue sample retrieved. The rod 60, which guides the cannula 48, includes a spring 86 and a cannula coupling 98 for engaging the cannula in the housing. The cannula 48 (FIG. 6) includes an aperture 66 in its base 68 for connecting to a protrusion or pin 100 (FIG. 19) on the cannula coupling 98. The cannula coupling 98 is pushed against the spring 86 by a cannula pushing member 115, which is attached to the cannula extension 56 (FIG. 8), until it reaches a position wherein the cannula 48 is spring loaded (i.e. in a spring compressed state) and ready for release. The spring loaded position is obtained when a second locking member 123 (FIGS. 15–18) on the cannula coupling 98 engages a first locking member 122 as explained hereinafter. Once the spring loaded position is obtained, a return spring 112 moves the cannula extension 56 back to its forward position (FIGS. 12–14). A spring stop 113 is included for providing a biasing force against the spring stop 113 when the cannula extension 56 is moved rearward.

The rod 58, which guides the stylet, includes a spring 62 and a stylet coupling 64 for engaging the stylet in the housing (FIGS. 19–21). The stylet coupling 64 also includes an actuating pin 11 6 (FIGS. 15–18) for striking a front projection on an actuating arm 110 thereby automatically releasing the cannula after the stylet has been fired. The stylet 48 (FIG. 6) includes an aperture 102 in its base 104 for connecting to a protrusion or pin 70 (FIG. 19) on the stylet coupling 64. The stylet coupling 64 is pushed against the spring 62 by a stylet pushing member 72, which is attached to the stylet extension 82 (FIG. 21), until it reaches a position wherein the stylet 48 is spring loaded (i.e. in a spring compressed state) and ready for release. The spring loaded position is obtained when a second locking member 117 (FIGS. 15–18) on the stylet coupling 64 engages a first locking member 118 as explained hereinafter. Once the stylet 48 is the spring loaded position, a bias spring 114 maintains the stylet extension 82 in the rearward position until the operator pushes it forward to release the stylet (FIGS. 12–14). A spring stop 111 is also included for providing a force against the bias spring 114 when the spring and the stylet extension is in its forward position. It is understood that no safety mechanism is necessary in the present invention as the locking of the stylet extension serves as a safety feature since a large amount of manual forward force and motion is required to overcome the force of spring 62 when firing the stylet. In FIGS. 15–18, once extension 82 is urged forward releasing second locking member 117 from first locking member 118 (a trip protrusion 120, which is attached to extension 82, deflects a stylet locking member protrusion 119), the actuating pin 116 of stylet coupling 64 strikes the front projection 125 (FIG. 18) of actuating arm 110 and pulls it slightly forward. This results in a back projection 110a of actuating arm 110 being urged against and deflecting a cannula locking member protrusion 124 thereby releasing the first locking member 122 of the cannula coupling 98 from the second locking member 123. Once the cannula 48 is released, the spring 86 urges the cannula 48 forward in a rapid motion severing the prolapsed tissue which resides in the needle notch.

Referring now to FIGS. 9 through 11, the locking lid 54 is shown. The locking lid 54 covers the bottom of the housing 52 and has a descending portion 74 having side walls 76 which provides the opening 44 for insertion of the needle set. The front of the locking lid includes a catch 78 on each side which engage a cut-out 80 (FIG. 1) located on the front of the housing 52. Once the needle set is inserted, the descending portion 74 is pushed up so that it is flush with the bottom of the housing 52 and the needle set is secured inside the housing by engagement of the catches 78 in cut-outs 80 on the front of the housing. The catches 78 are hook-shaped so as to allow the catches 78 to be easily urged into the cut-outs 80. Once in place, the front edge of the hook-shaped catches 78 snaps into locking the catches in the cut-outs.

At the front of the cannula extension 56, a pushing portion 94 (FIG. 8) is provided. The pushing portion 94 includes ribs 96 for enhanced friction between the user's thumb and the pushing portion during the biopsy procedure when the cannula extension is moved rearward. On top of the cannula extension 56, a number one (1) is indicated showing the sequence of actions required to take a tissue biopsy (FIGS. 12-14). The extension 56 is moved rearward in a first step. Located behind and axially of the slidable extension 56 near the front of the housing is the cannula coupling 98 for securing the cannula 48 and the cannula pushing member 115 (FIGS. 19–21) and for pushing the cannula coupling 98 against the spring 86. When the handle assembly is assembled, the cannula coupling 98 and the cannula pushing member 115 are located within the housing 52. The cannula coupling 98 includes a protrusion or pin 100 which is inserted into an aperture 66 (FIGS. 6–7) located on a base 68 of the cannula 48 as previously described heretofore.

Similar to the cannula extension 56, a pushing portion 88 (FIG. 8) is provided at the front of the stylet extension 82. The pushing portion 88 includes ribs 96 (FIG. 8) for enhanced friction between the user's thumb and the pushing portion when the stylet extension is moved rearward during the biopsy procedure. A second pushing portion 99 is also provided for single-handedly firing the stylet 46 forward, then sequentially the cannula 48, into the biopsy area. On top of the stylet extension 82, a number two (2) is indicated showing the sequence of actions required to take a tissue biopsy (FIGS. 12–14). The stylet extension 82 is moved rearward in a second step after the cannula extension 56 is moved rearward first. Located behind and axially of the stylet extension 82 near the front is a stylet coupling 64 for securing the stylet 46 and the stylet pushing member 72 (FIGS. 19–21) and for pushing the stylet coupling 64 against the spring 62. When the handle assembly is assembled, the stylet coupling 64 and the stylet pushing member 72 are located within the housing 52. The stylet coupling 64 includes a protrusion or pin 70 which is inserted into an aperture 102 (FIGS. 6–7) located on a base 104 of the stylet 46.

Considering FIGS. 15 through 18, in detail, these figures depict top cross-section views of the handle assembly 40 showing the operation of the internal parts and mechanisms associated with the cannula extension 56 and the stylet extension 82. FIG. 15 shows the mechanisms of the slidable extensions which move the stylet and the cannula. The stylet pushing member 72 and the cannula pushing member 115, which are attached to the stylet extension 82 and the cannula extension 56, are shown in a starting position, along with the stylet coupling 64 and the cannula coupling 98, respectively. FIG. 16 shows the cannula being forced rearward by the cannula extension 56 and the cannula pushing member 115 on the cannula extension 56 until the first locking member 122 engages the second locking member 123 on the cannula coupling member 98 and the cannula is cocked. FIG. 17 shows the stylet 46 being forced rearward by the stylet extension 82 and the stylet pushing member 72 on the stylet extension 82 until the first locking member 118 engages the second locking member 117 on the stylet coupling member 64 and the stylet 46 is cocked. FIG. 18 shows the trip protrusion 120 being moved forward by the stylet extension 82 until the stylet locking member protrusion 119 is deflected to the point of releasing the first locking member 118 from the second locking member 117 of the stylet coupling 64. The stylet of the needle set is then urged rapidly forward by the spring in order to pierce tissue. With regard to the firing of the cannula 48, the cannula 48 is actuated when the actuating pin 116 hits the front projection 125 of the actuating arm 110 pulling it forward, which then moves the back projection 110a of actuating arm 110 thereby deflecting the cannula locking member protrusion 124 to the point of releasing the first locking member 122 from the second locking member 123 of the cannula coupling 64. The cannula of the needle set is then urged rapidly forward by the spring in order to pierce tissue.

Considering FIGS. 19–21, in detail, these figures depict crosssection inside bottom views of the embodiment of the handle assembly 40. FIG. 19 shows the stylet coupling 98 and the cannula coupling 64 in the starting position. The protrusions or pins 70, 100 of stylet coupling 98 and the cannula coupling 64 are inserted into the apertures 66, 102 located on the bases of the stylet 46 and of the cannula 48, and thereby position the stylet 46 and cannula 48 relative to the housing 52 of the handle 40 (FIG. 22). The cannula extension 56 (FIG. 8) is connected to the cannula pushing member 115 and the stylet extension 82 is connected to the stylet pushing member 72. The rods 58, 60 are provided for guiding the stylet and the cannula in the housing 52 via the stylet coupling 64 and the cannula coupling 98, respectively. The spring 62 is also provided for powering the stylet when it severs the tissue captured in the notch of the stylet. Spring 86 provides power for the cannula. FIG. 20 shows the cannula coupling 98 being moved rearward at the point where the first locking member 122 engages the second locking member 123 (FIG. 16). FIG. 21 shows the stylet coupling 98 being moved rearward at the point where the first locking member 118 engages the second locking member 117.

Considering FIGS. 22–24, in detail, these figures depict bottom cross-section views of the handle assembly 40 including the needle set 42 showing the operation of the cannula extension 56 (FIG. 8), the stylet extension 82 (FIG. 8) and the related internal parts that detail the stages of the biopsy procedure. FIG. 22 shows the needle set 42 and the handle assembly 40 in the starting position. The apertures 66, 102 on both the stylet and the cannula are engaged with the protrusions or pins 70, 100 on the stylet coupling and cannula coupling, respectively. FIG. 23 shows the cannula 48 after the cannula has been moved rearward and the first locking member 122 has engaged the second locking member 123 (FIG. 16). FIG. 24 shows the assembly wherein the stylet 46 has been urged backward and remains in the spring loaded position ready for release.

As shown in FIGS. 25a–e, the needle set 42 is inserted into the handle assembly 40 in the descending portion 74 of the locking lid 54 which is then pushed upward and secured via the catch 78 and the cut-outs 80 located on each side of the locking lid and the front of the housing, respectively. In a single-handed operation shown in FIGS. 26a–d, the cannula extension 56 is moved rearward until the cannula 48 is in the spring loaded position and the first locking member 122 has engaged the second locking member 123 (FIG. 26b). The stylet extension 82 is then moved rearward until the stylet 48 is in the spring loaded position and the first locking member 118 has engaged the second locking member 117 (FIG. 26c). The stylet 46 and the cannula 48 are inserted into the patient near the biopsy area. The stylet 46 is then released into the biopsy area (FIG. 28d) by advancing the stylet extension 82 by pushing on the second pushing portion 99 or the back of pushing portion 88 with user's thumb so that the tissue is pierced and relaxes into the notch 50 of the stylet (shown in FIG. 26b). Once the stylet extension 82 is pushed forward by the user's thumb and the stylet advances, the cannula is then automatically actuated as explained hereinafter. The trip protrusion 120 which is connected to stylet 82 deflects the stylet locking member protrusion 119 thereby releasing the first locking member 118 from the second locking member 117 on the stylet coupling. Thereafter, the actuating pin 116 located on the stylet coupling hits the front projection 125 of actuating arm 110 and then the back projection 110a of the actuating arm deflects the cannula locking member protrusion 124. The cannula is released (the first locking member 122 of the cannula disengages the second locking member 123) and then rapidly moves forward so that the tissue in the notch is severed and retained in the notch of the stylet (FIG. 26d). The stylet and cannula are together disengaged from the biopsy site. The stylet 46 and the cannula 48 are both moved rearward by their respective extensions. The cannula 48 is then pressed rearward using the cannula extension 56 so that the tissue sample is exposed and may be removed (FIG. 28b). Moving the stylet extension 82 rearward reestablishes the stylet 46 and the cannula 48 in relation to each other in order to allow subsequent reinsertions into the biopsy area for additional tissue samples.

In another embodiment shown in FIGS. 27–30, the handle assembly 40 for the needle set 42 allows the user to obtain a tissue sample from a tissue mass of a predetermined size via an adjustable wheel 126 located on the rear end of the stylet extension 82. Details relating to the handle assembly including the adjustable wheel on the extension are described in Applicants' U.S. patent application Ser. No. 09/076,181 entitled "BIOPSY NEEDLE HANDLE", previously incorporated herein by reference. Similar to the embodiment described heretofore, the cannula extension 56 is urged rearward first. Then stylet extension 82 is urged rearward on the housing 52. Thereafter, the adjustable wheel 126 is turned to the desired depth. The adjustable wheel 126 allows the user to choose the parameters of the needle set 42 to be used to obtain optimal tissue sample for any given biopsy procedure. The adjustable wheel 126 is attached to the stylet extension 82 by a screw member 128. Located on the screw member 128 is a trip bar 130 (FIG. 31). When the adjustable wheel 126 is turned, the desired preset penetration depth of needle is obtained. The trip bar 130 includes a protrusion or tip 132 and moves forward along with the stylet extension 82. The wheel 126 sets the position of the protrusion or tip 132 relative to the stylet extension 82. The stylet extension, together with the trip bar 132 are pushed forward, thus urging the stylet 46 forward the preset length, until the trip bar protrusion or tip 132 interacts with the first locking member protrusion 119 (FIG. 15) as explained heretofore. Also provided on the top of the stylet extension is a window 134 which displays a corresponding numeric indicator of the desired set penetration depth. The penetration depth may be set from 13 mm to 21 mm (FIGS. 27–29) and is the distance that the needle set is urged forward into the biopsy area. It is understood that smaller and larger lengths can be possible with the same basic design as is understood by one skilled in the art.

Second Embodiment:

In yet another embodiment shown in FIGS. 32–47, wherein similar components in the second embodiment have the same numbering as in the first embodiment, the automated handle assembly 140 for the needle set 42 is preferably comprised of a metal material. It is understood that a metal material, such as aluminum, stainless steel, or a combination of both, is preferred. The material used in the handle assembly should allow for smooth slidable movement of the components in the handle assembly. The metal handle assembly may be fabricated by casting or machining, although it is understood that other methods of fabrication may be utilized. Such a metal handle assembly is designed to be used multiple times, with appropriate sterilization between each use.

Figure 37:
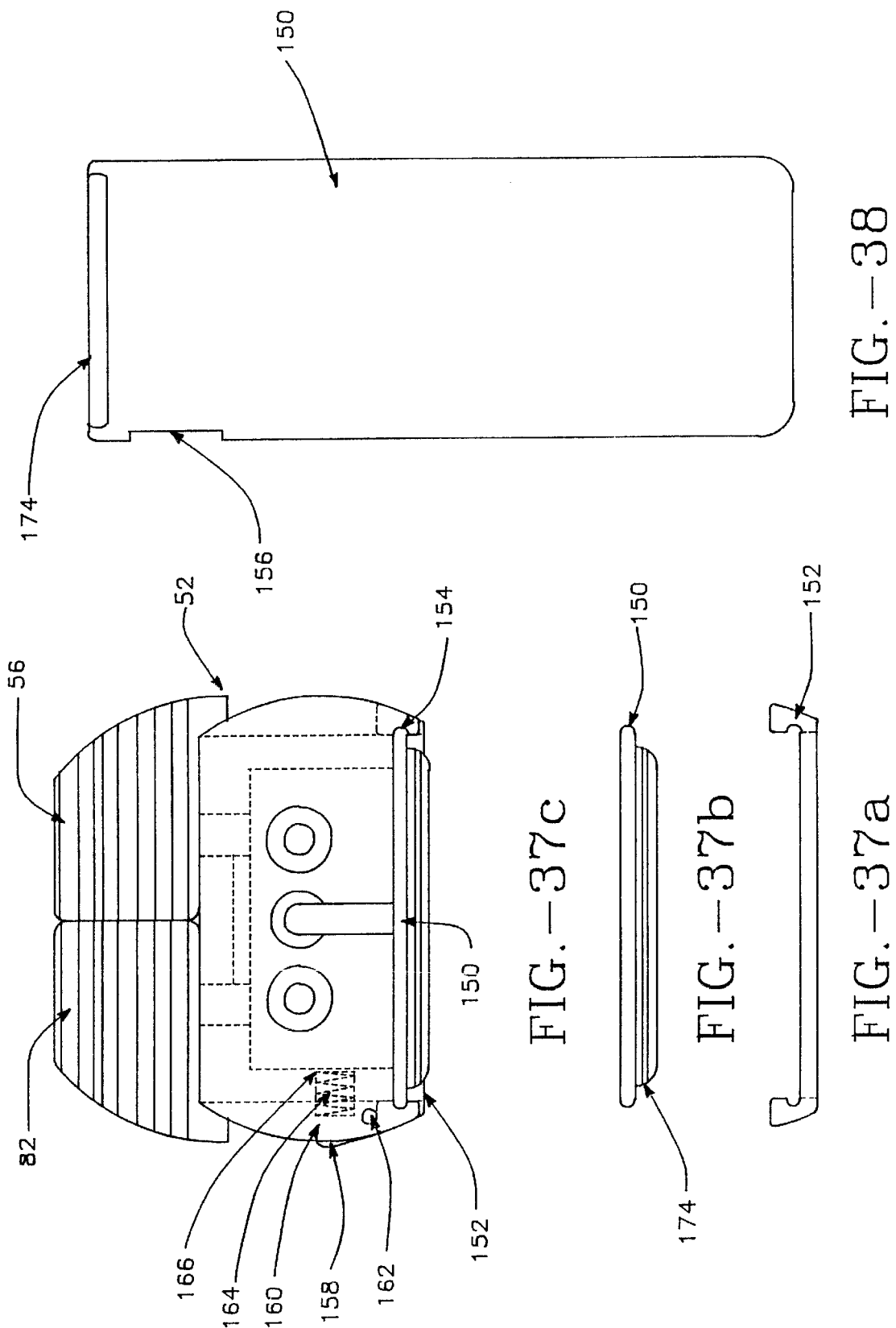
FIG. 37a is an end view of the fixed lid of the handle assembly of FIG. 32 according to the present invention.
FIG. 37b is an end view of the slidable lid of the handle assembly of FIG. 32 according to the present invention.
FIG. 37c is an end view of the embodiment of the handle assembly of FIG. 32 showing the fixed lid and the pivoting locking member engaging the slidable lid according to the present invention.
FIG. 37d is an end view of the embodiment of the handle assembly of FIG. 32 showing the fixed lid and the pivoting locking member disengaging the slidable lid according to the present invention.
Figure 38:
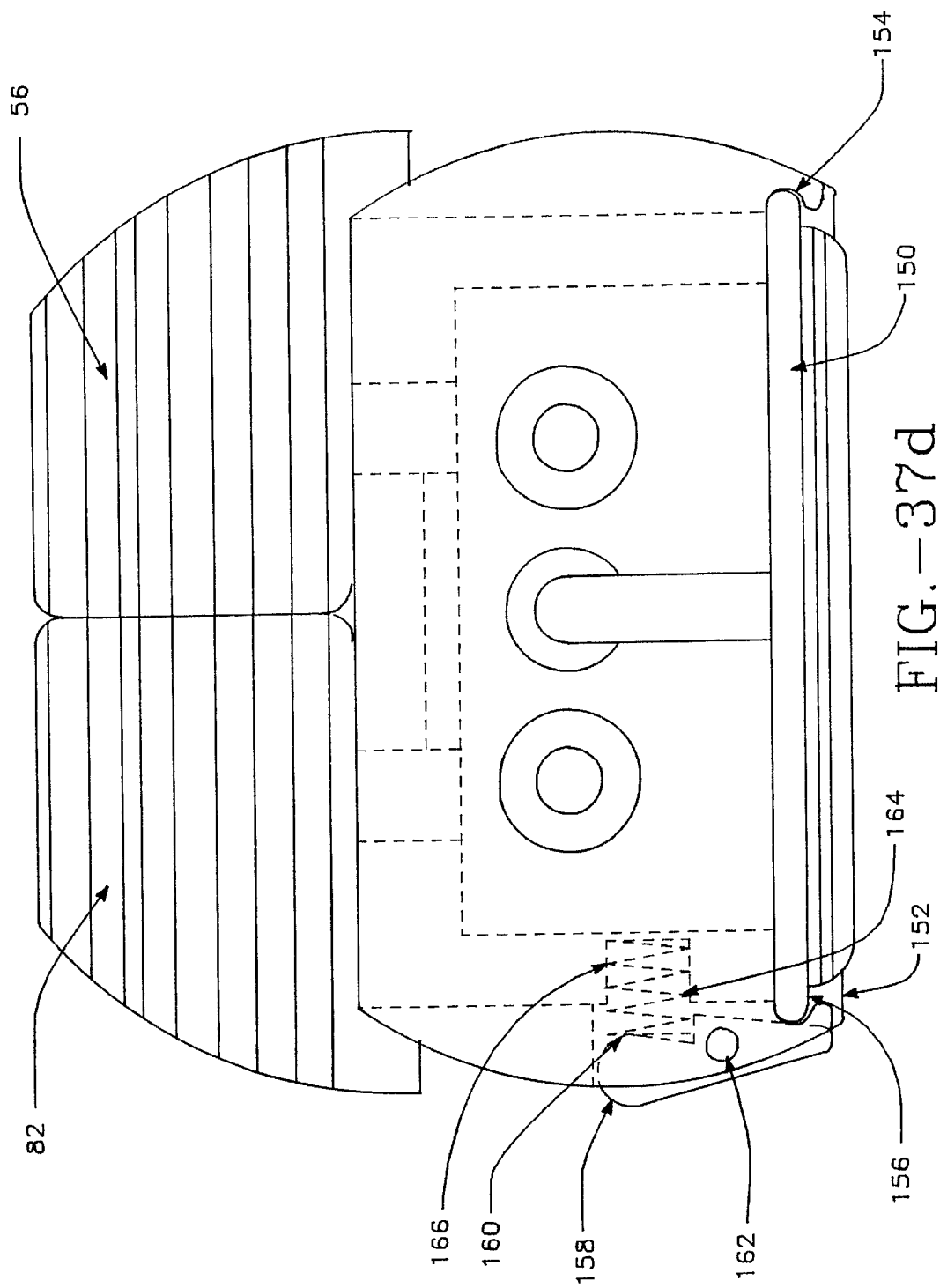
FIG. 38 is a bottom view of the slidable lid of the handle assembly of FIG. 32 according to the present invention.

In this embodiment, the needle set 42 is inserted into the housing 52 via a slidable lid 150 (FIGS. 37b, 38). The slidable lid 150 allows for insertion of the needle set in pre-cocked (FIGS. 32, 34) and cocked (FIGS. 33, 35) positions as explained hereinafter. The housing 52 includes a fixed cover 152 (FIG. 37a) on the bottom of the housing and the slidable lid 150 located within the housing parallel to the fixed cover 152. The slidable lid 150 is inserted into a slot 154 (FIG. 37c–d) which is located within the housing 52 in the bottom portion. The fixed cover 152 extends over approximately a one-third portion of the bottom of the back of the housing, thereby leaving an opening for insertion of the needle set 42 when the slidable lid 150 is in an open position (FIGS. 32–35). As shown in FIGS. 32 and 33, when the needle set is being inserted, the user must align the apertures 102, 66 (FIG. 32, 33) in the base of the stylet 104 and the base of the cannula 68 with the stylet coupling 64 and the cannula coupling 98, respectively.

Figure 36:
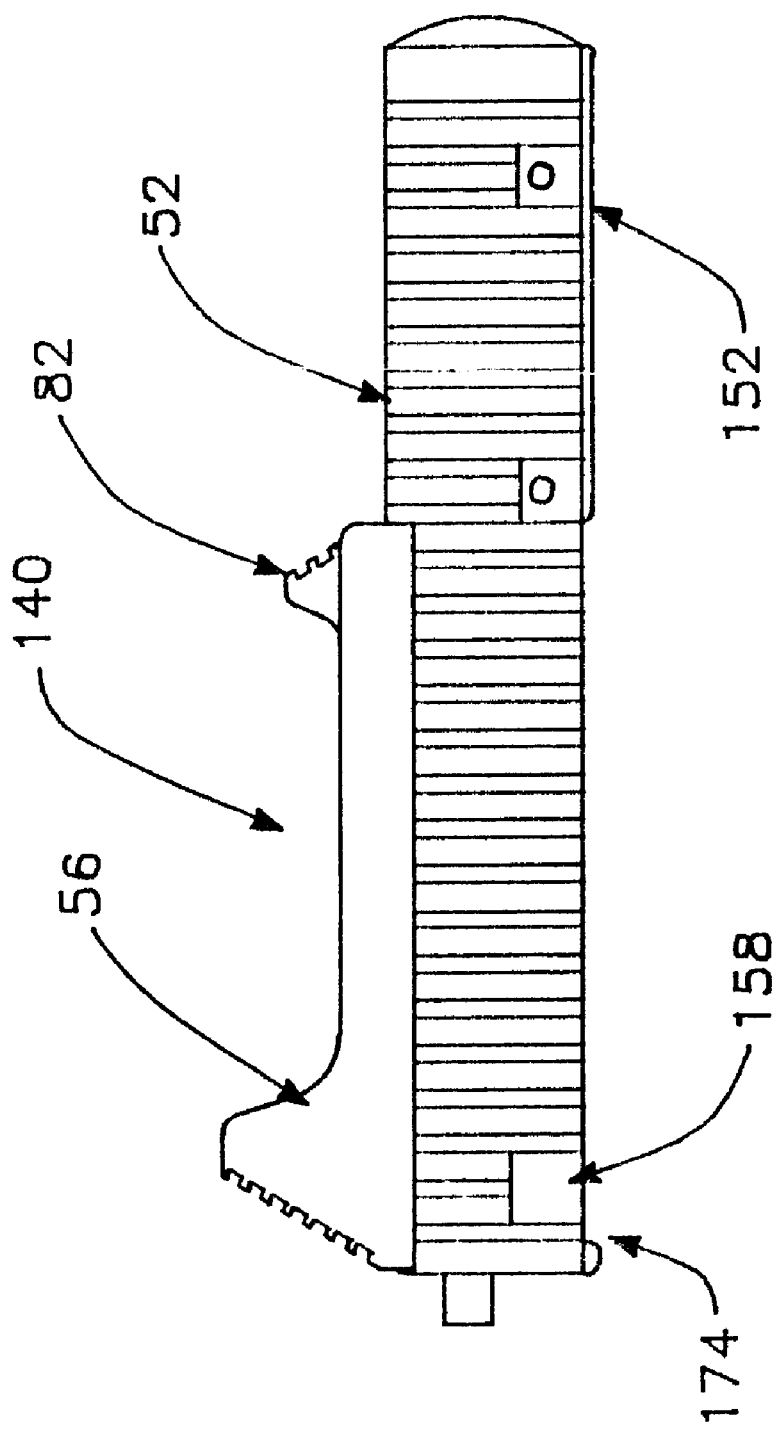
FIG. 36 is a side view of the embodiment of the handle assembly of FIG. 32 showing the slidable lid closed according to the present invention.

The slidable lid 150 is capable of being placed in three positions: open pre-cocked (FIGS. 32, 34), open cocked (FIGS. 33, 35), and closed (FIG. 36). In the open pre-cocked position, the opening is approximately one-third of the total length of the housing 52. In the open cocked position, the opening is approximately two-thirds of the total length of the housing. It may be preferable for a user to cock the metal handle assembly prior to insertion of the needle set. This is desirable in situations where the needle set has been inserted into a patient and the needle set is unable to support the weight of the metal handle assembly. Once in the cocked position, the metal handle assembly 140 is attached to the needle set 42 and ready to be actuated.

Figure 39:
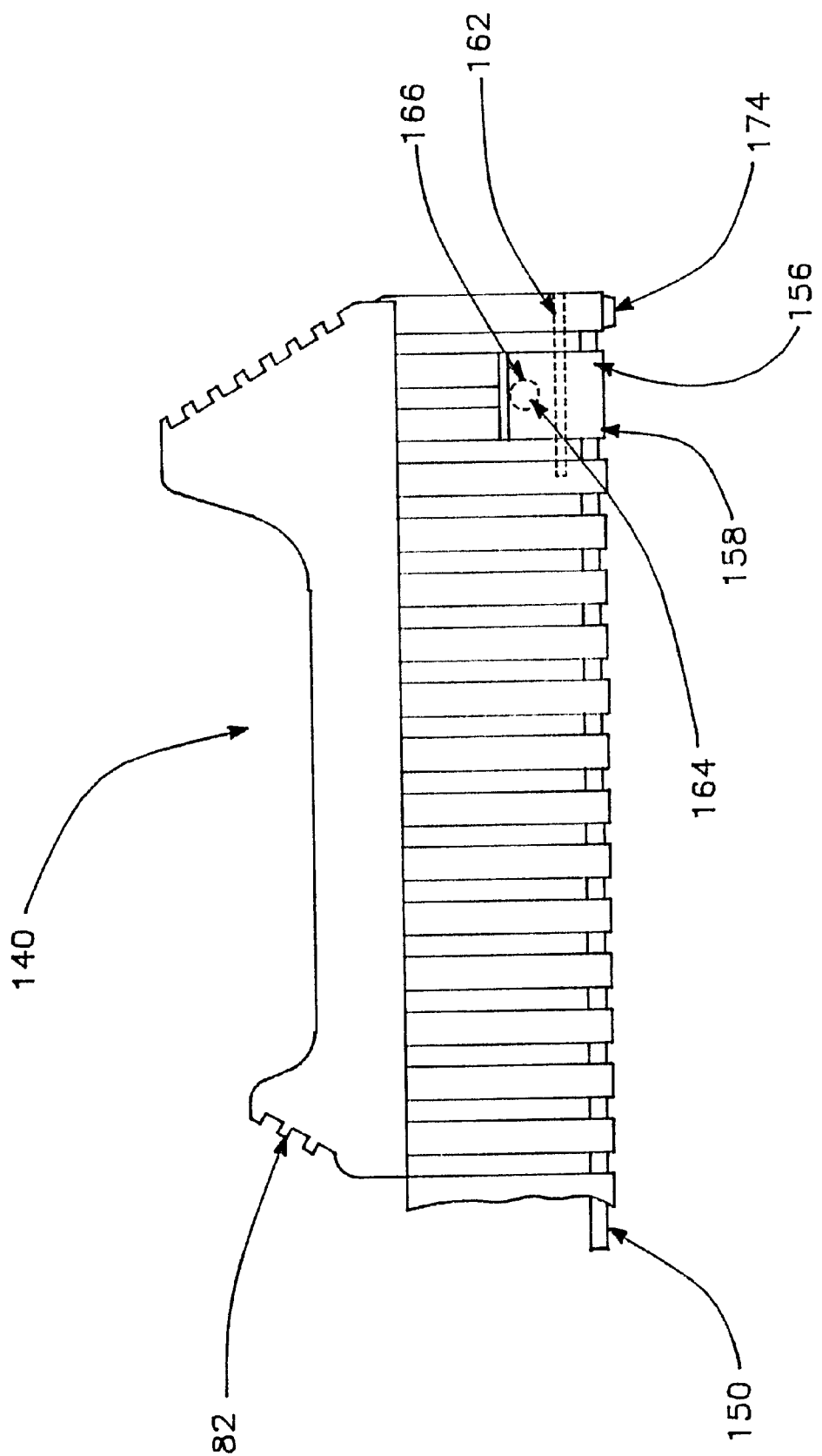
FIG. 39 is a side view of the embodiment of the handle assembly of FIG. 32 showing the details of the slidable lid, the pivoting locking member, and the pivot bar for locking the slidable lid in the closed position according to the present invention.

As shown in FIGS. 37–39, the slidable lid 150 includes a notch 156 (FIG. 38) located on one side of the slidable lid for locking the lid into the closed position after insertion of the needle set. The notch 156 is located at a front end of the slidable lid. The notch 156 is engaged by a pivoting locking member 158 (FIG. 39) located in a cavity 160 (FIG. 37c–d) in a side of the housing 52 near a front end of the housing 52. It is understood that the notch and the pivoting locking member may be placed in other locations of the slidable lid and housing, respectively, for locking the lid in a pre-cocked, a cocked, and the closed positions.

The pivoting locking member 158 pivots about a pivot bar 162 (FIGS. 37c–d, 39) which extends through the pivoting locking member 158 and the cavity 160 in the housing. A locking spring 164 (FIGS. 37c–d, 39), located in a bore 166 in the cavity 160, rests on a bottom portion of the pivoting locking member 158. The locking spring 164 provides a biasing force against the bottom portion of the pivoting locking member 158 causing the top portion of the pivoting locking member 158 to engage the notch 156 when the slidable lid reaches the appropriate place on the housing. When the slidable lid is locked and in the closed position, the bottom portion springs outward and remains extended out from the housing (FIG. 37c). To release the slidable lid from the pivoting locking member, the user pushes in on the bottom portion causing the top portion to moved outward from the notch (FIG. 37d), allowing the slidable lid to slide along the housing.

As shown in FIGS. 36–39, the slidable lid 150 also includes a lip member 174 for moving the slidable lid between the open and closed positions. It is understood that the features of the slidable lid may be incorporated into the embodiment of the plastic automated handle assembly and the semi-automated Biopsy Needle Handle previously incorporated herein by reference.

With reference to FIGS. 40–47, a spring-loaded cannula and stylet hook assembly is shown. The spring-loaded cannula and stylet hook assembly comprises a cannula hook 176, a stylet hook 178 and a hook spring 180 (FIGS. 41–43). The cannula hook 176 is a separate component and includes the first locking member 122 and the cannula locking member protrusion 124 as previously described above with respect to the first embodiment. Similarly, the stylet hook 178 is a separate component and includes the first locking member 118 of the stylet and the stylet locking member protrusion 119. The cannula hook 176 and the stylet hook 178 are joined together and to the housing with a fastener such as a pivot pin 182 and a flat head screw 184. The pivot pin 182 and flat head screw 184 are tightened sufficiently to secure the cannula hook 176 and the stylet hook 178 to the housing 52, but also allow for the pivoting movement of the hooks. The cannula hook 176 and stylet hook 178 both include bores which are located proximate the cannula locking member protrusion 124 and the stylet locking member protrusion 119. The hook spring 180 is inserted in both bores and maintains the cannula hook and the stylet hook biased away from each other. The hook spring 180 is extended when both extensions are locked and ready to be actuated and compressed after both extensions have been fired (FIG. 43). The hook spring 180 returns the cannula hook and the stylet hook back to their extended positions once the stylet extension and the cannula extension have been actuated and the needle set has been withdrawn from the patient.

Figure 40:
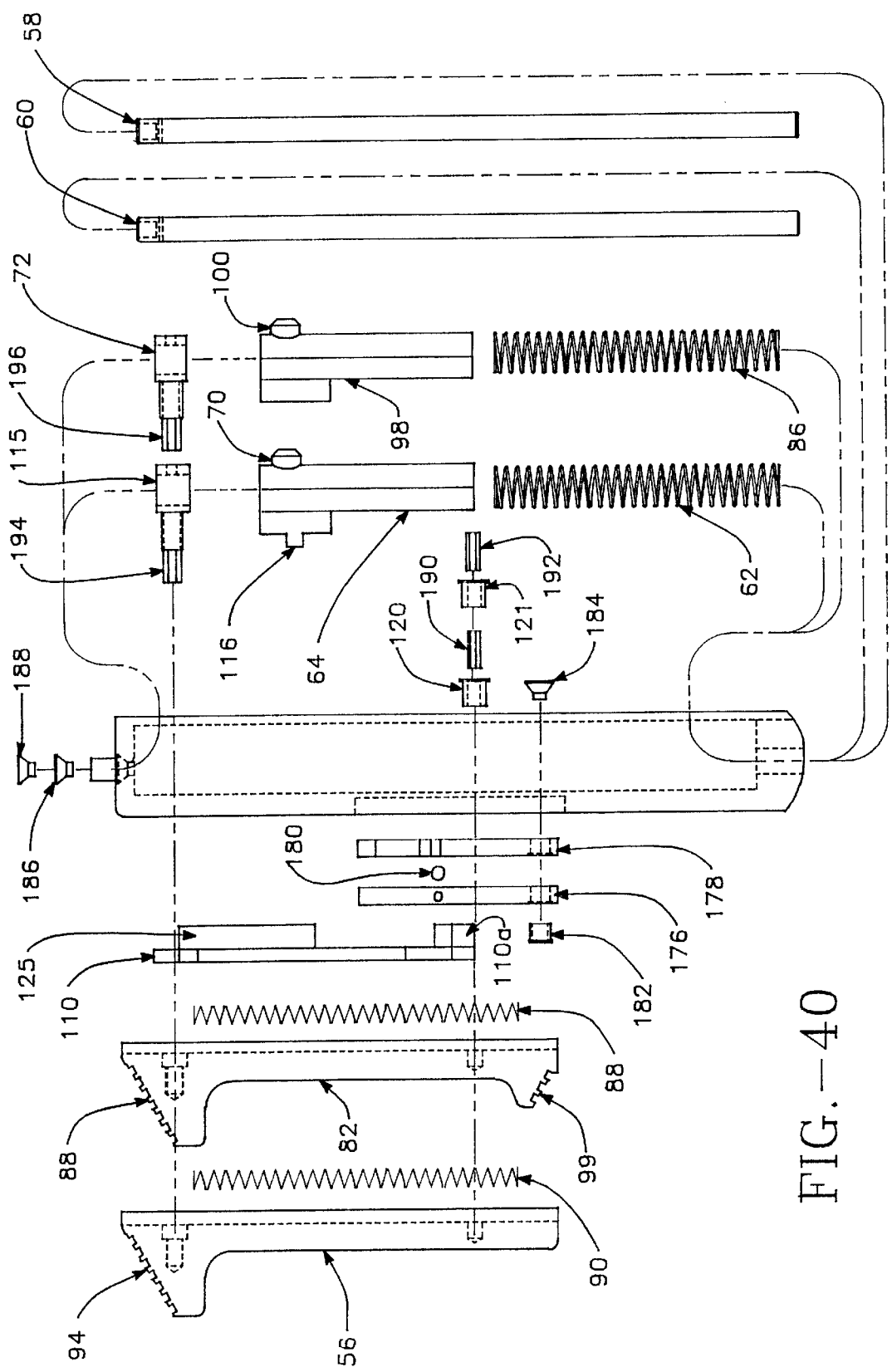
FIG. 40 is an exploded side view of the embodiment of the handle assembly of FIG. 32 according to the present invention.

Additionally, the rod 60 which guides the cannula and the rod 58 which guides the stylet are separate components detachable from the housing 52. The rods 60, 58 are secured to the housing 52 by flat head screws 186 and 188, respectively which are inserted through openings in the end of the housing (FIG. 40). Similarly, the cannula protrusion 121 (FIGS. 44–47), the trip protrusion 120, the cannula pushing member 115 and the stylet pushing member 72 are detachable from the cannula extension 56 and the stylet extension 82. The cannula protrusion 121 and the trip protrusion 120 are secured to the respective cannula and stylet extensions by fasteners 192 and 190 which are inserted into complementary openings in the extensions (FIG. 40). The cannula pushing member 115 and the stylet pushing member 72 are secured to the respective extension by connectors 194 and 196 which are also inserted into complementary openings in the extensions (FIG. 40).

It is understood that the cannula hook and stylet hook are preferably separate components since metal is less pliant than plastic and the hook spring together with the pivot pin allow for the in and out movement of the cannula hook and the stylet hook during the biopsy procedure. It is also understood that separate components including the rods, the cannula protrusion, the trip protrusion, the cannula pushing member and the stylet pushing member are preferred in order for an easier and effective fabrication process of the metal handle assembly. Moreover, the components are individually machined parts which are assembled as compared to being molded in the first embodiment of the handle assembly. Once the separate components are assembled, the components function in the same manner as in the first embodiment.

In operation, the locking lid is pushed into the open position and the needle set 42 is inserted into the handle assembly 140 in the pre-cocked position or cocked position. In a single-handed operation with the needle set inserted in the pre-cocked position, the cannula extension 56 is first moved rearward (FIG. 45) until the cannula 48 is in the spring loaded position and the first locking member 122 on the cannula hook 145 has engaged the second locking member 123 (FIG. 45). The stylet extension 82 is then moved rearward until the stylet 48 is in the spring loaded position and the first locking member 118 on the stylet hook 178 has engaged the second locking member 117 (FIG. 46). The stylet 46 and the cannula 48 are inserted into the patient near the biopsy area.

It is understood that the needle set may also be inserted into the patient at the biopsy area first before the needle set has been inserted into the handle assembly. The cannula extension and stylet extension are both moved rearward into the spring loaded position and the needle set is then inserted into the handle assembly in the cocked position (FIG. 33). Cocking the metal handle assembly prior to insertion of the needle set is preferable in situations where the needle set has been inserted into a patient and the needle set is unable to support the weight of the metal handle assembly.

After the handle assembly is in the cocked position with the needle set inserted, the stylet 46 is then released into the biopsy area (FIG. 47) by advancing the stylet extension 82 and pushing on the second pushing portion 99 or the back of pushing portion 88 with user's thumb so that the tissue is pierced and relaxes into the notch 50 (FIG. 8) of the stylet, as previously described. Once the stylet extension 82 is pushed forward by the user's thumb and the stylet advances, the cannula is then automatically actuated as explained hereinafter. The trip protrusion 120 which is connected to stylet extension 82 deflects the stylet locking member protrusion 119 thereby releasing the first locking member 118 on the stylet hook 178 from the second locking member 117 on the stylet coupling. Thereafter, the actuating pin 116 located on the stylet coupling hits the front projection 125 of actuating arm 110 and then the back projection 110a of the actuating arm deflects the cannula locking member protrusion 124 on the cannula hook 176. The cannula is released (the first locking member 122 of the cannula disengages the second locking member 123) and then rapidly moves forward so that the tissue in the notch is severed and retained in the notch of the stylet. The hook spring 180 is compressed since the cannula hook 176 and the stylet hook 178 have been actuated. The trip protrusion 120 maintains the stylet hook 178 pressed inward and the back projection 110a maintains the cannula hook 176 pressed inward. The stylet and cannula are together disengaged from the biopsy site. The stylet 46 and the cannula 48 are both moved rearward by their respective extensions at which point the hook spring 180 is decompressed and extended to its biasing position. The cannula 48 is then urged rearward using the cannula extension 56 so that the tissue sample is exposed and may be removed. Moving the stylet extension 82 rearward reestablishes the stylet 46 and the cannula 48 in relation to each other in order to allow subsequent reinsertions into the biopsy area for additional tissue samples.

Similar to the handle assembly made of plastic previously described and depicted in FIGS. 27–30, the metal handle assembly may include an adjustable wheel 126 on the rear end of the stylet extension 82 which allows the user to obtain a tissue sample from the tissue mass of a predetermined size. The adjustable wheel 126 is also metal and may be turned to the desired depth allowing the user to choose the parameters of the needle set. The metal handle assembly may also include a window 134 for displaying a corresponding numeric indicator of the set penetration depth. The procedure for obtaining the optimal tissue sample in a given biopsy procedure using the metal handle assembly is the same as the procedure for the plastic handle assembly described above and further description thereof is deemed unnecessary for a full understanding of the present invention.

It is understood that the metal handle assembly is sterilized after each use and reusable with the single patient use, disposable needle set.

Accordingly, the present invention provides for an inventive handle assembly and needle set which simplifies the biopsy procedure and which is easy to use and make. The handle assembly allows for manual manipulation to the utmost simplicity by incorporating the cocking of the cannula and stylet, the safety feature and the firing mechanism in a single assembly, thus allowing real single-handed operation without the need of separate components, buttons or slides to activate each of these actions. The disposable handle assembly thus affords an uncomplicated design allowing the handle to be inexpensive to fabricate and more compact. Similarly, the metal handle assembly affords an uncomplicated design allowing the handle to be automatic, inexpensive, more compact and reusable.

It is understood that the handle assembly and a needle set having a particular needle length (for obtaining a tissue sample of a predetermined size) may be preassembled when manufactured and made available to a physician as a packaged and sterilized device. This would be advantageous to the physician who routinely uses one particular sized needle set in a biopsy procedure.

Although the invention has been described in detail herein, it should be understood that the invention is not limited to the embodiment herein disclosed. Various changes, substitutions and modifications may be made thereto by those skilled in the art without departing from the spirit or scope of the invention as described and defined by the appended claims.

Industrial Applicability

The advantages of the present invention include a handle assembly for a needle set which single-handedly and automatically captures a tissue sample from a tissue mass. The handle assembly incorporates the cocking of the cannula and stylet, the safety feature and the firing mechanism in a single assembly without the need of separate components, buttons or slides to activate each of these actions.

Other features, aspects and objects of the invention can be obtained from a review of the figures and the claims.

It is to be understood that other embodiments of the invention can be developed and fall within the spirit and scope of the invention and claims.

I claim:

1. A biopsy handle capable of receiving a needle set assembly having a stylet adapted for piercing and storing a tissue sample and a cannula adapted for severing and trapping the tissue sample, the biopsy handle comprising:
   a housing including a slidable lid adapted for accepting the needle set;
   a first actuator slidably attached to the housing and adapted for selectively positioning the cannula relative to the housing;
   a second actuator slidably attached to the housing and adapted for selectively positioning the stylet relative to the housing; and
   said first actuator and said second actuator both including an element which is adapted to allow said first actuator and said second actuator to be slid in a forward and a reverse direction with respect to the housing in order to move the cannula and the stylet relative to the housing using a single hand of a use.

2. The biopsy handle of claim 1, wherein the biopsy handle is made of metal and reusable.

3. The biopsy handle of claim 1, further including:
   a fixed lid located on a portion of a bottom of said housing and adjacent to said slidable lid, wherein said slidable lid can be moved from an open position in order to accept the needle set into said housing to a closed and locked position in order to lockingly contain the needle set in the housing.

4. The biopsy handle of claim 3 wherein:
   said slidable lid include a notch and said housing includes a cavity having a pivoting locking member therein, said notch receiving said pivoting locking member for securing the slidable lid in place when locking the needle set in said housing in said closed position.

5. The biopsy handle of claim 4 wherein:
   said housing includes a spring for urging said pivoting locking member into said notch.

6. A biopsy handle capable of receiving a needle set assembly having a stylet adapted for piercing and storing a tissue sample and a cannula adapted for severing and trapping the tissue sample, the biopsy handle capable of receiving the needle set in a pre-cocked position and a cocked position, the biopsy handle comprising:

a housing having a fixed bottom lid covering a portion of the housing;

a slidable lid, said slidable lid mounted within the housing and parallel to said fixed bottom lid; and said slidable lid is positionable such that said slidable lid is open to a first position in the pre-cocked position and said slidable lid is open to a second position in the cocked position.

7. The biopsy handle of claim 6, further comprising:

a first guide secured to said housing;

a second guide secured to said housing;

a first actuator slidably mounted on said housing;

a second actuator slidably mounted on said housing;

a first pin associated with said first guide;

a second pin associated with said second guide;

said first pin adapted to engage a cannula of a needle set;

said second pin adapted to engage a stylet of a needle set;

a first spring associated with said first guide and said first pin;

a second spring associated with said second guide and said second pin;

a first pushing member that is associated with said first pin in order to urge said first pin relative to said first guide and against said first spring;

a second pushing member that is associated with said second pin in order to urge said second pin relative to said second guide and against said second spring; and said first pin and said first pushing member operatively associated with said first actuator such that as said first actuator slides relative to said housing, said first pin and said first pushing member move relative to said housing and along said first guide in order to urge the cannula into a first operable position.

8. The biopsy handle of claim 7 further including:

said housing having a first locking member;

said first pin having a second locking member;

and with the cannula in the first operable position such that said first pin is urged against said first spring, said first locking member engages said second locking member in order to lock said first pin in the first operable position relative to said housing.

9. The biopsy handle of claim 8 further including:

said second pin and said second pushing member operatively associated with said second actuator such that as said second actuator slides relative to said housing, said second pin and said second pushing member move relative to said housing and alone said second guide in order to urge the stylet into a second operable position;

said housing having a third locking member;

said second pin having a fourth locking member;

and with the stylet in the second operable position such that said second pin is urged against said second spring, said third locking member engages said fourth locking member in order to lock said second pin in the second operable position relative to said housing.

10. The biopsy handle of claim 8 further including:

a trip pin;

said trip pin associated and movable with said second actuator;

said trip pin being capable of contacting said third locking member in order to release said fourth locking member and thereby allow said second spring to move said second pin and thus the stylet relative to said housing.

11. The biopsy handle of claim 10 further including:

an actuating pin;

said actuating pin associated and movable with said second actuator;

said actuating pin being capable of contacting an actuating arm, said actuating arm also being capable of contacting said first locking member in order to release said second locking member and thereby allow said first spring to move said first pin and thus the cannula relative to said housing.

12. The biopsy handle of claim 6 wherein:

said slidable lid is positionable in a closed position, said slidable lid includes a notch and said housing includes a cavity having a pivoting locking member therein, said notch receiving said pivoting locking member for securing said slidable lid in place when locking the needle set in said housing in said closed position.

13. The biopsy handle of claim 6, wherein the biopsy handle is reusable and made of metal.

14. The biopsy handle of claim 6, wherein said slidable lid is open approximately one-third of a housing length in the pre-cocked position and said slidable lid is open approximately two-thirds of the housing length in the cocked position.

15. A biopsy handle capable of receiving a needle set assembly having a stylet adapted for piercing and storing a tissue sample and a cannula adapted for severing and trapping the tissue sample, the biopsy handle capable of receiving the needle set in a pre-cocked position and a cocked position, the biopsy handle comprising:

a housing having a fixed bottom lid covering a portion of the housing;

a slidable lid, said slidable lid mounted within the housing and parallel to said fixed bottom lid;

a first extension having a first pushing member, said first extension slidably mounted on said housing;

a second extension having a second pushing member, said second extension slidably mounted on said housing;

a first hook;

a second hook;

a biasing member in communication with said first hook and said second hook;

a first rod secured to said housing;

a second rod secured to said housing;

a first pin in communication with said first pushing member and said first rod, said first pin having a first locking member;

a second pin in communication with said second pushing member and said second rod, said second pin having a second locking member;

wherein said first pushing member urges said first pin relative to said first rod sliding said first extension relative to said housing for urging the cannula into a first operable position, said first hook engaging said first locking member in said first operable position, and said second pushing member urges said second pin relative to said second rod sliding said second extension relative to said housing for urging the stylet into a second operable position, said second hook engaging said second locking member in said second operable position.

16. The biopsy handle of claim 15, wherein the needle set is inserted in the pre-cocked position before said first operable position and said second operable position have been achieved.

17. The biopsy handle of claim 15, wherein the needle set is inserted in the cocked position after said first operable position and said second operable position have been achieved.

18. The biopsy handle of claim 15, wherein the slidable lid is open approximately one-third of a housing length in the pre-cocked position and the slidable lid is open approximately two-thirds of the housing length in the cocked position.

19. The biopsy handle of claim 15 wherein:
said slidable lid is positionable in a closed position, said slidable lid includes a notch and said housing includes a cavity having a pivoting locking member therein, said notch receiving said pivoting locking member for securing said slidable lid in place when locking the needle set in said housing in said closed position.

20. The biopsy handle of claim 15, wherein the biopsy handle is reusable and made of metal.

\* \* \* \* \*